(12) United States Patent
Matsuzaki et al.

(10) Patent No.: US 8,034,117 B2
(45) Date of Patent: *Oct. 11, 2011

(54) BONE REPLACEMENT MATERIAL

(75) Inventors: Hiromi Matsuzaki, Tokyo (JP); Yoshie Tominaga, Saitama (JP)

(73) Assignees: Hoya Corporation, Tokyo (JP); Hiromi Matsuzaki, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/596,303

(22) PCT Filed: Dec. 9, 2004

(86) PCT No.: PCT/JP2004/018359
§ 371 (c)(1),
(2), (4) Date: Jan. 26, 2007

(87) PCT Pub. No.: WO2005/055886
PCT Pub. Date: Jun. 23, 2005

(65) Prior Publication Data
US 2007/0156247 A1    Jul. 5, 2007

(30) Foreign Application Priority Data
Dec. 9, 2003    (JP) .................................. 2003-410873

(51) Int. Cl.
*A61F 2/28* (2006.01)
(52) U.S. Cl. ................. 623/23.61; 623/16.11; 623/17.11
(58) Field of Classification Search ............... 623/17.11, 623/18.11, 23.5, 23.56, 16.11, 17.16, 23.51, 623/23.61–23.63
See application file for complete search history.

(56) References Cited

U.S. PATENT DOCUMENTS

| 5,645,596 | A |   | 7/1997 | Kim et al. |
| 6,139,585 | A | * | 10/2000 | Li ............................... 623/23.57 |
| 6,183,515 | B1 | * | 2/2001 | Barlow et al. ............... 623/16.11 |
| 6,187,329 | B1 | * | 2/2001 | Agrawal et al. ............... 424/426 |

(Continued)

FOREIGN PATENT DOCUMENTS
EP    0107476    5/1984
(Continued)

OTHER PUBLICATIONS

English Language Abstract of JP 2003-135583.

(Continued)

*Primary Examiner* — Corrine M McDermott
*Assistant Examiner* — Megan Wolf
(74) *Attorney, Agent, or Firm* — Greenblum & Bernstein, PLC

(57) ABSTRACT

Bone replacement material to be used by being packed into a bone defective part, wherein the bone replacement material consists essentially of a calcium phosphate based compound and is formed into a pellet and satisfies both of the following conditions (I) and (II): (I) porosity is equal to or less than 75%; and (II) collapsing strength is equal to or more than 15 Mpa. The pellet has a roughly polyhedral shape and is defined by a plurality of surfaces including a pair of opposite, non-parallel surfaces and a surface adjoining to the pair of opposite, non-parallel surfaces, one of the opposite, non-parallel surfaces being inclined at a predetermined angle with respect to the other of the opposite, non-parallel surfaces. The one of the opposite, non-parallel surfaces is non-adjoined with the other of the opposite, non-parallel surfaces in the pellet. The other of the opposite, non-parallel surfaces is perpendicular to the surface adjoining to the pair of opposite, non-parallel surfaces.

12 Claims, 16 Drawing Sheets

U.S. PATENT DOCUMENTS

| | | | |
|---|---|---|---|
| 6,264,695 B1 * | 7/2001 | Stoy | 623/17.16 |
| 6,293,971 B1 * | 9/2001 | Nelson et al. | 623/23.63 |
| 6,387,130 B1 * | 5/2002 | Stone et al. | 623/17.16 |
| 6,458,162 B1 * | 10/2002 | Koblish et al. | 623/23.51 |
| 6,511,510 B1 * | 1/2003 | de Bruijn et al. | 623/23.56 |
| 6,725,083 B1 * | 4/2004 | Burbank et al. | 600/431 |
| 6,905,516 B1 | 6/2005 | Lemaitre et al. | |
| 7,238,209 B2 * | 7/2007 | Matsuzaki et al. | 623/23.61 |
| 2002/0026242 A1 * | 2/2002 | Boyle et al. | 623/17.11 |
| 2002/0165616 A1 | 11/2002 | Heide et al. | |
| 2003/0060892 A1 * | 3/2003 | Richter et al. | 623/23.51 |
| 2003/0109883 A1 | 6/2003 | Matsuzaki et al. | |
| 2003/0120351 A1 * | 6/2003 | Tofighi et al. | 623/23.62 |
| 2004/0010314 A1 | 1/2004 | Matsuzaki et al. | |
| 2004/0024465 A1 * | 2/2004 | Lambrecht et al. | 623/17.16 |
| 2004/0052829 A1 * | 3/2004 | Shimp | 424/423 |
| 2005/0038517 A1 * | 2/2005 | Carrison et al. | 623/17.16 |

FOREIGN PATENT DOCUMENTS

| | | | |
|---|---|---|---|
| JP | 61-170471 | | 8/1986 |
| JP | 2-001508 | | 1/1990 |
| JP | 2-1508 | * | 1/1990 |
| JP | 8-10276 | | 1/1996 |
| JP | 2001-79024 | | 3/2001 |
| JP | 2001-206787 | | 7/2001 |
| JP | 2002-113090 | | 4/2002 |
| JP | 2003-135583 | * | 5/2003 |
| JP | 2003-169811 | | 6/2003 |
| JP | 2003-210567 | | 7/2003 |
| WO | 96/39202 | | 12/1996 |
| WO | 00/71178 | | 11/2000 |

OTHER PUBLICATIONS

English Language Abstract of JP 2003-210567.
English Language Abstract of JP 2003-169811.
English language Abstract of JP 2001-79024, Mar. 27, 2001.
English language Abstract of JP 2002-113090, Apr. 16, 2002.
English language Abstract of JP 8-10276, Jan. 16, 1996.
English language Abstract of JP 2001-206787, Jul. 31, 2001.

* cited by examiner

BONE REPLACEMENT MATERIAL

TECHNICAL FIELD

This invention relates to a bone replacement material.

BACKGROUND ART

Collapse of a vertebral body as a result of external injuries (trauma) or osteoporosis is referred to as a vertebral body compression fracture. In the method that is known for the treatment of this kind of fracture, the collapsed vertebral body is repaired by filling the inside thereof with a filler (such as a bone replacement material) through a vertebral arch using a transpedicular technique.

In this treatment method, a collapsed vertebral body is first returned to a substantially original shape, that is, a collapsed vertebral body is reduced, whereby a cavity (a born defective part) is created therein. A filler such as a bone replacement material is then packed into the cavity to repair the vertebral body, or a filler is packed into the cavity to push a fragile spongy bone aside so that the inside of the collapsed vertebral body is reinforced.

Conventionally, in such a treatment method, the inside of the collapsed vertebral body is filled with a granular bone replacement material by directly packing it from an opening formed in the collapsed vertebral body (see JP-A No. 2003-169811, for example).

However, it is troublesome to fill the inside of the collapsed vertebral body with a large amount of the granules of the bone replacement material each having an irregular shape. Further, in the case where the inside of the collapsed vertebral body is filled with a granular bone replacement material using a cylindrical member, a hollow passage of the cylindrical member is likely to be clogged with the bone replacement material due to its irregular shape, so that there is a case that it is difficult to smoothly perform such a filling operation. Furthermore, in the case where the conventional bone replacement material (comprised of granules having irregular shapes) is used, the granules of the bone replacement material introduced into the cavity of the vertebral body is likely to remain near the vicinity of an opening of the distal end of the cylindrical member, thus it is difficult to fill the cavity with a sufficient amount of the bone replacement material. Furthermore, even when the cavity is filled with a large amount of the bone replacement material, it is difficult to increase the filling ratio sufficiently due to the presence of many gaps among the granules. Moreover, each granule of the granular bone replacement material has an irregular shape as described above, and thus some of the granules are formed with protrusions on their surfaces. Such granules are likely to be broken when a load is applied thereto, so that the volume of the vertebral body is decreased. As a result, it is difficult to keep the result of the operation over a long period of time.

Further, in addition to the above method, there is another method which uses a bone replacement material (bone cement) that has fluidity when it is introduced into a vertebral body but will be hardened in the vertebral body. However, when such a material is used, there is a risk that the material will flow out from the vertebral body to thereby damage adjacent nerves or block blood flow, thus problems still remain in its safeness.

DISCLOSURE OF THE INVENTION

It is an object of the present invention to provide a bone replacement material by which a packing or filling operation to a bone defective part can be carried out smoothly, reliably and safely.

The above-mentioned object can be achieved by the present invention which is defined in the following items (1) to (21).

(1) A bone replacement material to be used by being packed into a bone defective part, wherein the bone replacement material is formed into a pellet defined by a plurality of surfaces and satisfies at least one of the following conditions (I) and (II):

(I) porosity is equal to or less than 75%; and
(II) collapsing strength is equal to or more than 15 Mpa.

Use of such a bone replacement material makes it possible to carry out a packing operation of the bone replacement material into a bone defective part smoothly, reliably and safely.

Further, since the bone replacement material is formed into a pellet having a predetermined shape, a packing operation of the bone replacement material using a cylindrical member having a hollow passage can be made easily.

Furthermore, since the bone replacement material has sufficient strength, even in the case where the bone replacement material is packed into a bone defective part to which external stress is applied, the shape thereof can be maintained stably for a long period of time.

(2) The pellet of the bone replacement material described in the above-mentioned item (1) may be formed into a roughly prismatic shape.

This makes it possible to carry out the packing operation of the bone replacement material into a bone defective part more smoothly, reliably and safely. Further, since a filling ratio of the bone replacement material into a bone defective part can be increased, it is possible to maintain the result of the operation for a long period of time.

(3) The pellet of the bone replacement material described in the above-mentioned item (1) may be formed into a roughly hexahedral shape.

This also makes it possible to increase a filling ratio of the bone replacement material into a bone defective part, thereby enabling the result of the operation to be maintained for a long period of time.

(4) The pellet of the bone replacement material described in the above-mentioned item (3) may be formed into a rectangular solid a part of which is cut off.

This also makes it possible to carry out the packing operation of the bone replacement material into a bone defective part more smoothly, reliably and safely. Further, since a filling ratio of the bone replacement material into a bone defective part can be increased, it is possible to maintain the result of the operation for a long period of time.

(5) The pellet of the bone replacement material described in the above-mentioned item (1) may be formed into a roughly pentahedral shape.

This also makes it possible to increase a filling ratio of the bone replacement material into a bone defective part, thereby enabling the result of the operation to be maintained for a long period of time.

(6) The pellet of the bone replacement material described in the above-mentioned item (5) may be formed into a triangular prism shape a part of which is cut off.

This also makes it possible to carry out the packing operation of the bone replacement material into a bone defective part more smoothly, reliably and safely. Further, this also makes it possible to increase a filling ratio of the bone replacement material into a bone defective part, thereby enabling the result of the operation to be maintained for a long period of time.

(7) The pellet of the bone replacement material described in the above-mentioned item (1) may be formed into a roughly trihedral shape.

This also makes it possible to increase a filling ratio of the bone replacement material into a bone defective part, thereby enabling the result of the operation to be maintained for a long period of time.

(8) The pellet of the bone replacement material described in the above-mentioned item (7) may be formed into a cylinder solid a part of which is cut off.

This also makes it possible to carry out the packing operation of the bone replacement material into a bone defective part more smoothly, reliably and safely. Further, this also makes it possible to increase a filling ratio of the bone replacement material into a bone defective part, thereby enabling the result of the operation to be maintained for a long period of time.

(9) In the bone replacement material described in the above-mentioned item (1), each pellet having a roughly polyhedral shape is defined by a plurality of surfaces including a pair of opposite surfaces, in which one of the opposite surfaces is inclined with respect to the other surface at a predetermined angle.

This also makes it possible to carry out the packing operation of the bone replacement material into a bone defective part more smoothly, reliably and safely. Further, this also makes it possible to increase a filling ratio of the bone replacement material into a bone defective part, thereby enabling the result of the operation to be maintained for a long period of time.

(10) In the bone replacement material described in the above-mentioned item (9), the predetermined angle is preferably in the range of 10 to 60°.

This also makes it possible to carry out the packing operation of the bone replacement material into a bone defective part more smoothly, reliably and safely. Further, this also makes it possible to increase a filling ratio of the bone replacement material into a bone defective part, thereby enabling the result of the operation to be maintained for a long period of time.

(11) In the bone replacement material described in the above-mentioned item (1), each pellet of the roughly polyhedral shape is defined by a plurality of edges having different lengths, in which the length of the longest edge is preferably in the range of 5 to 10 mm.

This also makes it possible to carry out the packing operation of the bone replacement material into a bone defective part more smoothly, reliably and safely. Further, this also makes it possible to increase a filling ratio of the bone replacement material into a bone defective part, thereby enabling the result of the operation to be maintained for a long period of time.

(12) In the bone replacement material described in the above-mentioned item (1), each pellet of the roughly polyhedral shape is defined by a plurality of edges having different lengths, in which the length of the shortest edge is preferably in the range of 2 to 5 mm.

This also makes it possible to carry out the packing operation of the bone replacement material into a bone defective part more smoothly, reliably and safely. Further, a filling ratio of the bone replacement material into a bone defective part can also be increased, thereby enabling the result of the operation to be maintained for a long period of time.

(13) In the bone replacement material described in the above-mentioned item (1), the volume of each pellet of the bone replacement material is preferably in the range of 13 to 239 $mm^3$.

This also makes it possible to carry out the packing operation of the bone replacement material into a bone defective part more smoothly, reliably and safely. Further, this also makes it possible to increase a filling ratio of the bone replacement material into a bone defective part, thereby enabling the result of the operation to be maintained for a long period of time.

(14) In the bone replacement material described in the above-mentioned item (1), each pellet of the bone replacement material may have been subjected to a chamfering processing.

This makes it possible to prevent the bone replacement material from undesirably damaging anatomy when the packing operation is carried out.

(15) In the bone replacement material described in the above-mentioned item (1), the bone replacement material is preferably used in a state that a number of pellets of the bone replacement material are introduced into a cavity of the bone defective part and they are aggregated therein.

This also makes it possible to increase a filling ratio of the bone replacement material into a bone defective part, thereby enabling the result of the operation to be maintained for a long period of time.

(16) In the bone replacement material described in the above-mentioned item (1), the bone replacement material is adapted to be packed into a cavity of the bone defective part using a cylindrical member having a hollow passage.

This also makes it possible to increase a filling ratio of the bone replacement material into a bone defective part, thereby enabling the result of the operation to be maintained for a long period of time.

(17) In the bone replacement material described in the above-mentioned item (1), the bone replacement material may be mainly formed of ceramics.

This makes it possible to improve affinity to living bodies.

(18) In the bone replacement material described in the above-mentioned item (17), the ceramics is preferably formed of calcium phosphate based compound.

This makes it possible to improve affinity to living bodies further.

(19) In the bone replacement material described in the above-mentioned item (18), the Ca/P ratio of the calcium phosphate based compound is preferably in the range of 1.0 to 2.0.

This also makes it possible to improve affinity to living bodies further.

(20) In the bone replacement material described in the above-mentioned item (1), the bone replacement material is adapted to be packed into a bone defective part formed in one or more bones such as vertebral body, ilium, scapula, humerus, ulna, radius, femur, tibia and fibula.

Although each of these bones has a relatively large size, the bone replacement material of the present invention can be packed into a bone defective part in these bones effectively with a high filling ratio.

(21) In the bone replacement material described in the above-mentioned item (1), each pellet of the bone replacement material 1 is formed into a roughly polyhedral shape which is defined by a plurality of surfaces including a pair of opposite surfaces in which one of the opposite surfaces is inclined with respect to the other surface at a predetermined angle, and when a plurality of pellets of the bone replacement material are introduced and packed into a cavity in the bone defective part using a cylindrical member having a hollow passage, each pellet of the bone replacement material is inserted into the hollow passage of the cylindrical member such that the inclined surface of the pellet faces the inclined surface of the adjacent pellet, whereby each pellet of the bone replacement material is pushed out in various directions from the hollow passage of the cylindrical member.

According to this, when a plurality of pellets of the bone replacement material are continuously introduced into the cavity in the bone defective part, the introduced pellets can be dispersed in different directions and uniformly filled in the cavity. Further, the bone replacement material introduced into the cavity of the vertebral body is unlikely to remain near an opening of the cylindrical member, thus it is possible to pack a sufficient amount of the bone replacement material into the cavity.

The invention also provides for a bone replacement material to be used by being packed into a bone defective part, wherein the bone replacement material consists essentially of a calcium phosphate based compound and is formed into a pellet and satisfies both of the following conditions (I) and (II): (I) porosity is equal to or less than 75%; and (II) collapsing strength is equal to or more than 15 Mpa. The pellet has a roughly polyhedral shape and is defined by a plurality of surfaces including a pair of opposite, non-parallel surfaces and a surface adjoining to the pair of opposite, non-parallel surfaces, one of the opposite, non-parallel surfaces being inclined at a predetermined angle with respect to the other of the opposite, non-parallel surfaces. The one of the opposite, non-parallel surfaces is non-adjoined with the other of the opposite, non-parallel surfaces in the pellet. The other of the opposite, non-parallel surfaces is perpendicular to the surface adjoining to the pair of opposite, non-parallel surfaces. The predetermined angle is in the range of 20 to 40°. The pellet of the roughly polyhedral shape is defined by a plurality of edges having different lengths, in which the length of the longest edge is in the range of 5 to 10 mm and the length of the shortest edge is in the range of 2 to 5 mm. The volume of the pellet of the bone replacement material is in the range of 13 to 239 mm$^3$. The bone replacement material is adapted to be packed into a cavity of the bone defective part using a cylindrical member having a hollow passage. When a plurality of pellets of the bone replacement material are introduced and packed into the cavity in the bone defective part using the cylindrical member, each pellet of the bone replacement material is inserted into the hollow passage of the cylindrical member such that the inclined surface of the pellet faces the inclined surface of the adjacent pellet, whereby each pellet of the bone replacement material is pushed out in various directions from the hollow passage of the cylindrical member. The plurality of pellets are configured to be pushed into the cavity in the bone defective part using the cylindrical member after being placed into the hollow passage of the cylindrical member. The pellet is formed free of a through hole being provided therethrough.

BEST MODE FOR CARRYING OUT THE INVENTION

Hereinbelow, preferred embodiments of a bone replacement material according to the present invention will be described in detail with reference to the accompanying drawings.

Figure 1:
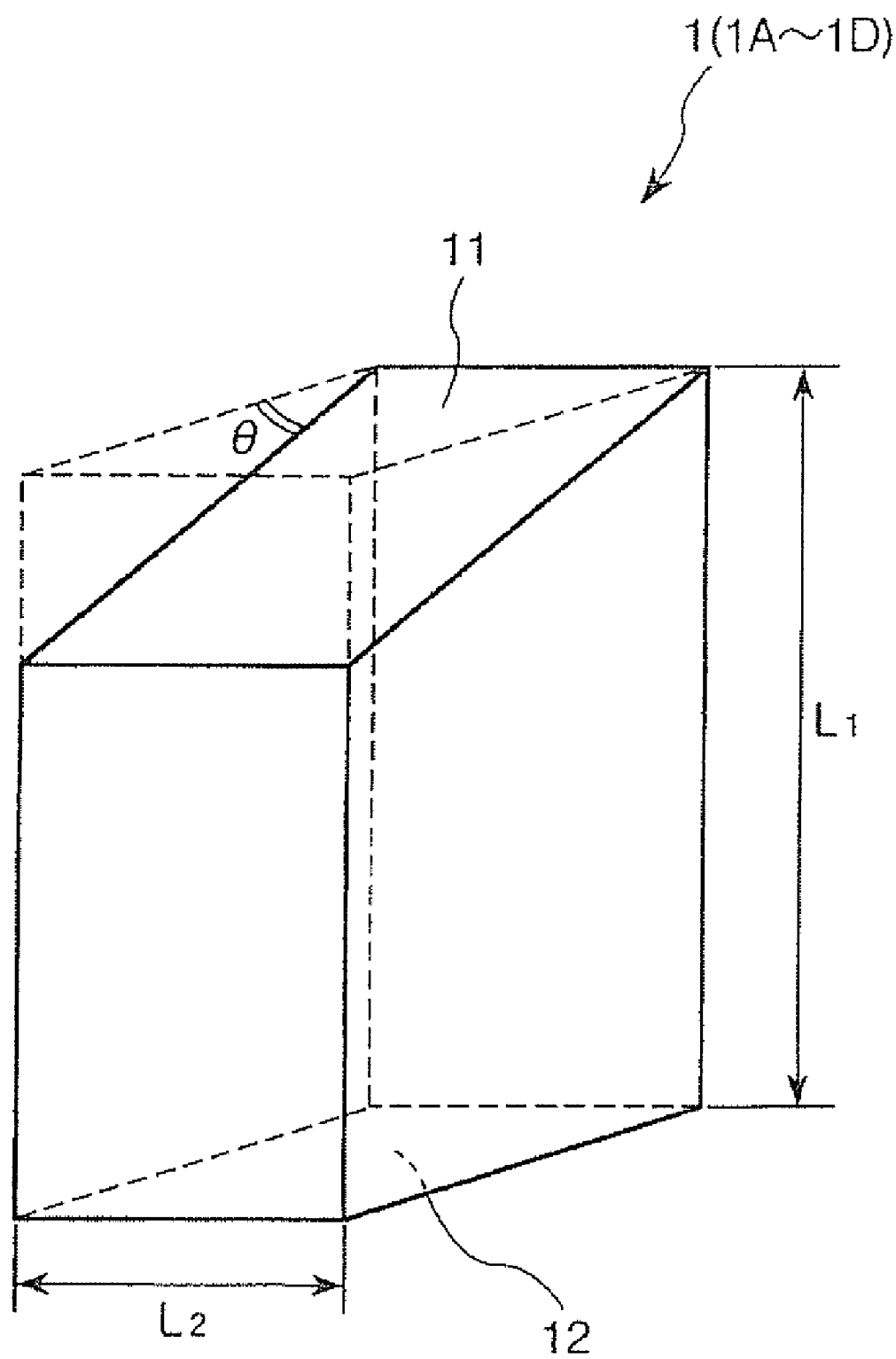
FIG. 1 is a perspective view which shows a preferred embodiment of a bone replacement material according to the present invention.

FIG. 1 is a perspective view which shows a preferred embodiment of a bone replacement material according to the present invention. The bone replacement material of the present invention is used by being packed into a bone defective part.

In this regard, it is to be noted that the term "bone defective part" in this specification means a cavity formed in a bone due to various causes such as external injuries, an operation for removal of a tumor, decreased bone density due to osteoporosis, or combination of these causes.

The bone replacement material of the present invention is suitably used for filling a bone defective part formed in one or more of bones such as vertebral body (centrum) ilium, scapula, humerus, ulna, radius, femur, tibia and fibula. Although each of these bones has a relatively large size, a bone defective part formed in these bones can be filled with the bone replacement material of the present invention effectively with a high filling ratio.

Hereinafter, a description will be made with regard to the case where the bone replacement material of the present invention is used for repairing a collapsed vertebral body (that is, for a treatment of a vertebral body compression fracture).

As shown in FIG. 1, the bone replacement material of the present invention 1 (1A, 1B, 1C and 1D) is formed into a pellet or a small block having a roughly polyhedral shape defined by a plurality of surfaces.

In the conventional treatment for repairing a vertebral body compression fracture, a roughly spherical (granular) bone replacement material is used. When such a conventional granular bone replacement material is used, a number of granules are packed within a cavity of a vertebral body in a state that each granule is in contact with adjacent other granules through small contacting areas due to its spherical shape. Therefore, the packed granules are in an unstable state within the vertebral body, thus displacement is likely to occur when a load is applied. When such displacement of the granules occurs, density of the packed bone replacement material becomes nonuniform at various positions inside the vertebral body. In other words, the cavity of the vertebral body will have a portion where an amount of the packed bone replacement material is insufficient. As a result, the volume of the vertebral body is decreased due to a load applied thereto, so that there is a case that the result of the operation can not be obtained sufficiently.

In contrast with the conventional bone replacement material descried above, the bone replacement material 1 of the present invention is formed into a pellet or small block having a roughly polyhedral shape defined by a plurality of surfaces, such a problem as involved in the conventional bone replacement material will be unlikely to occur. Specifically, according to the present inventions adjacent bone replacement materials 1 are in surface to surface contact with each other so that they are held or fixated stably. This realizes a load withstanding capacity. Therefore, even when the bone replacement material is used in a site where a load is applied, satisfactory packing condition can be maintained inside the cavity of the vertebral body without displacement for a long period of time.

Further, by forming the bone replacement material 1 into a pellet having a roughly polyhedral shape defined by a plurality of surfaces, it becomes possible to increase the filling ratio in the cavity of the vertebral body, that is, it is possible to reduce the space occupied by gaps. This makes it possible to suppress the volume of the vertebral body from being decreased after the operation, so that it becomes possible to maintain the result of the operation for a long period of time.

Furthermore, by forming the bone replacement material into a pellet having such a shape as mentioned above, it also becomes possible to effectively avoid an undesirable situation that the bone replacement material remains near an opening of a cylindrical member 51 which is described later. This makes it possible to pack a sufficient amount of the bone replacement material into a cavity of a vertebral body. Further, when this bone replacement material is used, there is less possibility that the hollow inner passage of the cylindrical member will be clogged with the bone replacement material, so that a packing operation of the bone replacement materials can be carried out smoothly and reliably.

In addition to the above, it is preferred that the bone replacement material 1 of the present invention satisfies either the following condition (I) or (II), and more preferably satisfies the both of them.

(I) The porosity of the bone replacement material 1 is preferably equal to or less than 75%, more preferably equal to or less than 50%, and even more preferably equal to or less than 30%. By setting the porosity of the bone replacement material 1 within such a range, the load withstanding capacity of the bone replacement material 1 can be made sufficiently high. Therefore, such a bone replacement material 1 can be suitably used in a site to which a load is applied.

Further, by setting the porosity of the bone replacement material 1 to a relatively high value within the above range (equal to or more than 50%, for example), osteoblast cells (bone cells) are allowed to enter the inside of the bone replacement material 1 easily. The bone replacement material 1 then becomes a scaffold for the osteoblast cells, whereby making it possible to accelerating growth of the osteoblast cells. As a result of this, it is possible to accelerate new bone formation, namely it is possible to contribute to early bone formation. Therefore, the bone replacement material 1 is suitably used in a bone defective part in which bone union is prioritized.

In this regard, in a case where the porosity of the bone replacement material 1 is larger than the above upper limit value, strength of the bone replacement material 1 is lowered depending on a constituent material thereof.

(II) The collapsing strength of the bone replacement material 1 is preferably equal to or more than 15 MPa, more preferably equal to or more than 30 Mpa, and even more preferably equal to or more than 150 Mpa. This makes it possible to make the load withstanding capacity of the bone replacement material 1 sufficiently high.

In this regard, in a case where the collapsing strength of the bone replacement material 1 is less than the above lower limit value, if such a bone replacement material 1 is packed into a site such as a vertebral body to which large pressing force (external stress) is applied, the bone replacement material 1 itself is collapsed in an early stage, whereby making it difficult to obtain sufficient operation effect.

The pellet-type bone replacement material 1 of the present invention can have various shapes so long as they have a roughly polyhedral shape defined by a plurality of sufaces. However, preferably, the bone replacement material 1 is formed into a pellet having a roughly prismatic shape (a part of which may be removed or cut off), more preferably, it is formed into a pellet having a roughly hexahedral shape (a part of which may be removed or cut off), and even more preferably, it is formed into a pellet a roughly rectangular solid shape (a part of which may be removed or cut off). If the bone replacement material 1 of the present invention is formed into a pellet having any one of the above mentioned shapes, the results stated above will become more conspicuous.

Further, in the present invention, it is preferred that the bone replacement material is formed into a pellet having a roughly polyhedral shape which is defined by a plurality of surfaces including a pair of opposite surfaces, in which one of the opposite surfaces is inclined with respect to the other surface at a predetermined angle as shown in FIG. 1 As will be described later in more detail, if each pellet of the bone replacement material is formed into a shape having such inclined opposite surfaces, the pellets of the bone replacement material 1 are dispersed inside a cavity of a vertebral body (a bone defective part) effectively when they are packed into the cavity, thereby enabling to further increase the filling ratio of the bone replacement material 1. The embodiment shown in FIG. 1 is an example of a pellet of the bone replacement material 1. As shown in the drawing, the pellet of the bone replacement material 1 is formed into a roughly rectangular solid in which a part thereof is removed or cut off so that one of the opposite surfaces 11 is inclined with respect to the other surface 12 at an angle θ.

The above-mentioned angle θ is preferably in the range of 10 to 60°, and more preferably in the range of 20 to 40°. If the angle θ is smaller than the lower limit value, there is a case that the effect obtained by the inclined surfaces can not be exhibited sufficiently. On the other hand, if the angle θ is larger than the upper limit value, sharp protrusions are formed on the bone replacement material so that chipping is likely to occur when a load is applied thereto.

Further, in the bone replacement material of the present invention, the length $L_1$ of the longest edge of each pellet is preferably in the range of 5 to 10 mm, and more preferably in the range of 5 to 7 mm. if the length $L_1$ of the longest edge is shorter than the lower limit value, a volume of each pellet of the bone replacement material becomes small, thus load withstanding capacity is lowered. On the other hand, the length $L_1$ of the longest edge is longer than the upper limit values desirable dispersion of the bone replacement material 1 is difficult to occur in the vertebral body.

Furthermore, in the bone replacement material of the present invention, the length $L_2$ of the shortest edge of each pellet is preferably in the range of 2 to 5 mm, and more preferably in the range of 3 to 4 mm. If the length $L_2$ of the shortest edge is shorter than the lower limit value, a volume of each pellet of the bone replacement material becomes small, thus load withstanding capacity is lowered. On the other hand, the length $L_2$ of the shortest edge is longer than the upper limit value, packing operation through a vertebral arch becomes difficult.

Moreover, in the present invention, the volume of each pellet of the bone replacement material is preferably in the range of 13 to 239 mm$^3$, and more preferably in the range of 40 to 100 mm$^3$. If the volume of each pellet of the bone replacement material is smaller than the lower limit value, the volume of each pellet of the bone replacement material becomes too small, and thus load withstanding capacity is also lowered. On the other hand, if the volume of each pellet of the bone replacement material is larger than the upper limit value, desirable dispersion is difficult to occur in the vertebral body (in the bone defective part).

The bone replacement material 1 of the present invention may be comprised of various pellets having different sizes and shapes depending on cases (body shapes of patients).

Further, in the bone replacement material 1 of the present invention, it is preferred that each pellet is subjected to chamfering processing. By subjecting each pellet to chamfering processing, it is possible to prevent the bone replacement material 1 from undesirably damaging anatomy when the packing operation is carried out or in a state that a vertebral body (a bone defective part) is filled with the bone replacement material 1.

Further, the bone replacement material 1 of the present invention is preferably formed of a material that can be used as a biomaterial.

Examples of materials that can be used for the biomaterial include various kinds of ceramics such as alumina, zirconia, calcium phosphate-based compound, and the like. Among these materials, calcium phosphate-based compound is preferred. This is because, since a calcium phosphate-based compound remains stably in a living body over a long period of time, it is particularly suitable for use as a biomaterial.

Examples of such a calcium phosphate-based compound include hydroxy apatite $(Ca_{10}(PO_4)_6(OH)_2)$, TCP $(Ca_3(PO_4)_2)$, $Ca_2P_2O_7$, $Ca(PO_3)_2$, $Ca_{10}(PO_4)_6F_2$, $Ca_{10}(PO_4)_6Cl_2$, DCPD$(CaHPO_4.2H_2O)$, $Ca_4O(PO_4)_2$, and the like, and one kind of or a mixture of two or more kinds of these calcium phosphate-based compounds may be employed.

In particular, a calcium phosphate-based compound having a Ca/P ratio of 1.0-2.0 is preferably used. By setting the Ca/P ratio to 1.0-2.0, the bone replacement material can have a Ca/P ratio closer to that of a bone tissue of a living body, so that it is being existed inside the living body for a long period of time.

Figure 2:
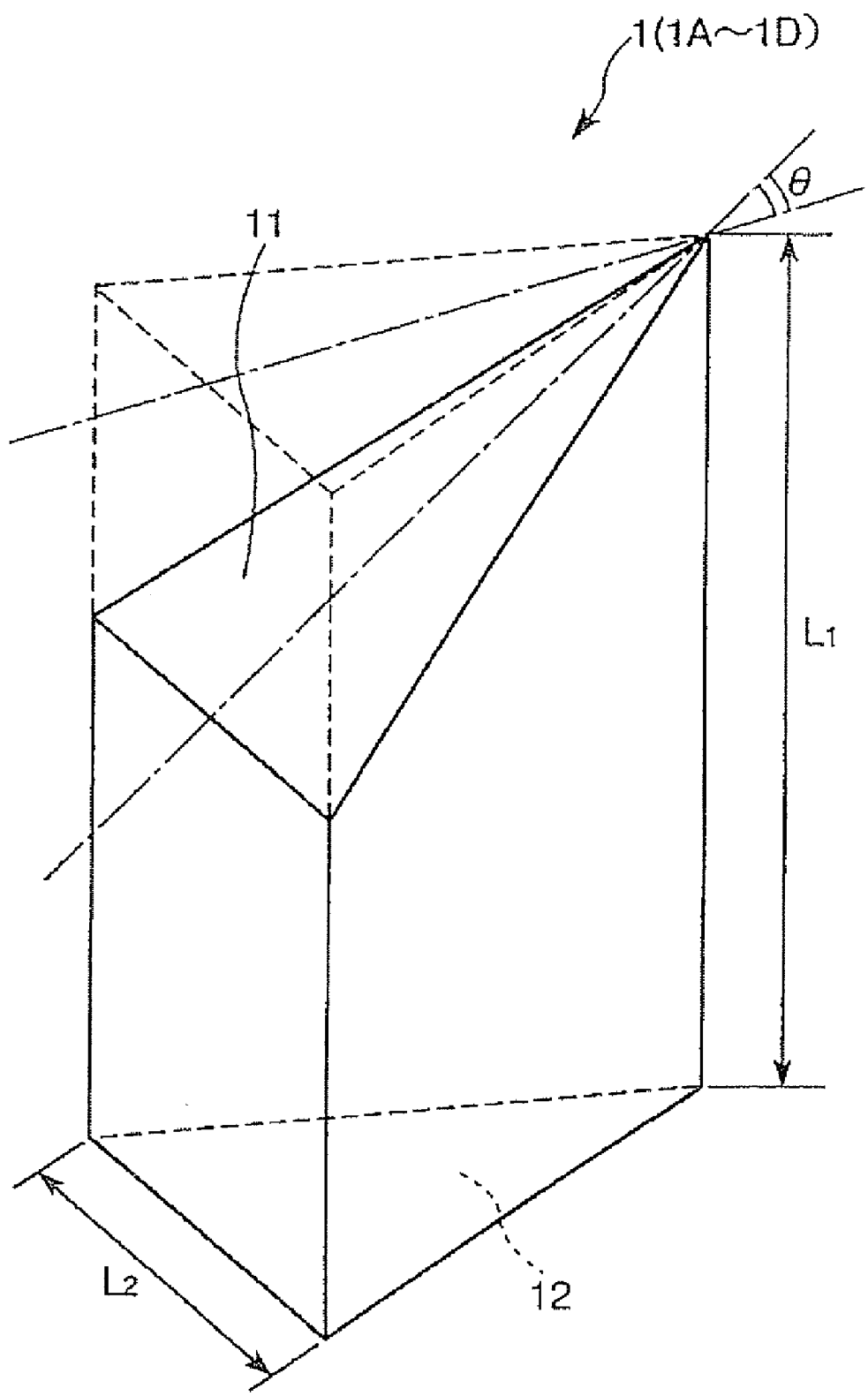
FIG. 2 is a perspective view which shows another embodiment of a bone replacement material according to the present invention.
Figure 3:
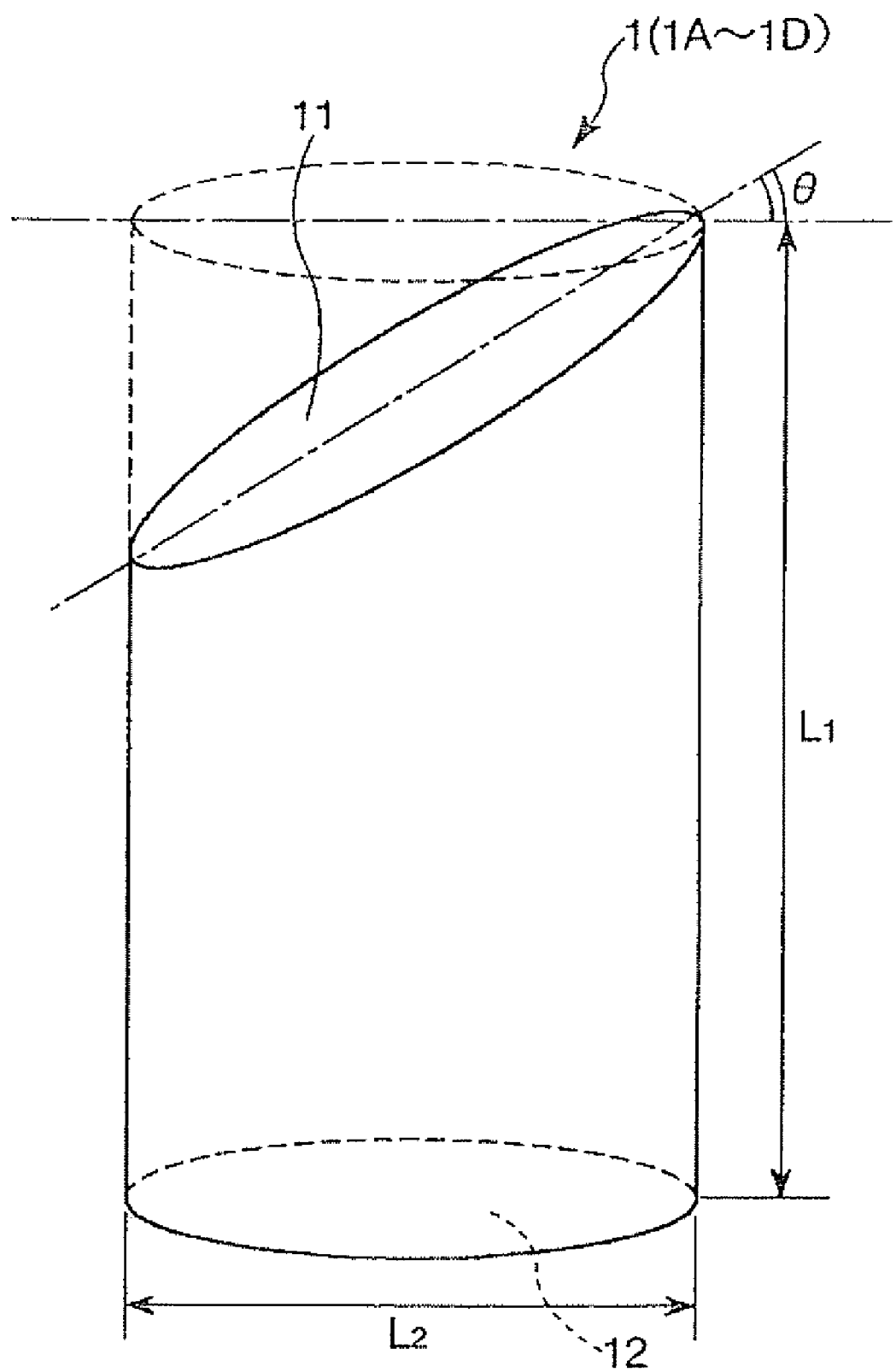
FIG. 3 is a perspective view which shows other embodiment of a bone replacement material according to the present invention.

Next, a description will be made with regard to other embodiments of a pellet of the bone replacement material 1. FIG. 2 and FIG. 3 are perspective views which show other examples of a pellet of the bone replacement material 1.

Hereinbelow, a description will be made with regard to differences between each of the pellets of the bone replacement material 1 shown in FIGS. 2 and 3 and the pellet shown in FIG. 1, and a description with regard to the overlapping points therebetween will be omitted.

A pellet of the bone replacement material 1 shown in FIG. 2 is formed into a roughly pentahedral shape (preferably, triangular prism shape) in which a part thereof is removed or cut off.

According to the bone replacement material 1 shown in FIG. 2, it is possible to obtain the same function and effect as those obtained in the bone replacement material 1 shown in FIG. 1. In particular, since the pellet shown in FIG. 2 is formed into a triangular prism shape (a part of which may be removed or cut off), namely has a finite form, it is possible to carry out a packing operation using a cylindrical member.

A pellet of the bone replacement material 1 shown in FIG. 3 is formed into a roughly trihedral shape (preferably, cylindrical shape) in which a part thereof is removed or cut off.

According to the bone replacement material 1 shown in FIG. 3, it is possible to obtain the same function and effect as those obtained in the bone replacement material 1 shown in FIG. 1. In particular, since a side surface of the pellet shown in FIG. 3 is formed into a continuous curved surface having no edge portion, it is possible to prevent the bone replacement material 1 from undesirably damaging anatomy more reliably when a packing operation is carried out or in a state that a vertebral body (a bone detective part) is filled with the bone replacement material 1.

The manufacturing method of the bone replacement material 1 is not particularly limited to any specific one, but it can be manufactured in the following manner in the case where a ceramics material is used as a constituent material thereof, for example.

Firstly, a ceramics slurry is obtained through a well-known method.

Next, a water-soluble polymer is added to the ceramics slurry, and it is then agitated to thereby form air bubbles therein.

Next, the thus obtained ceramics slurry is poured into a mold having a predetermined shape and then dried to obtain a compact.

Next, the thus obtained compact is processed using a general-purpose processing machine so as to have a desired shape as the bone replacement material 1 and the thus processed compact is then sintered or baked. In this way, the desired bone replacement material 1 is obtained.

In such a manufacturing method of the bone replacement material 1, the porosity of the bone replacement material 1 can be set to a desired value by appropriately setting a synthesis condition of a raw material powder (e.g. a diameter of primary particle, a dispersion state of a primary particle, and the like), a condition of raw material powder (e.g. an average particle diameter, preliminarily sintered or not, with or without a grinding process, and the like), a condition when forming air bubbles in the ceramics slurry by agitating it (kind of surfactant, agitation rate, and the like), a sintering condition (a sintering atmosphere, a sintering temperature, and the like) and the like.

Hereinafter, a description will be made with regard to one example of the method for packing the bone replacement material 1 of the present invention into a vertebral body.

FIGS. 4 to 10 are schematic views for explaining the method for packing or introducing the bone replacement material 1 of the present invention. Further, FIG. 11 is a schematic view showing a vertebral body to which a treatment for repairing a vertebral body compression fracture has been carried out. FIGS. 12 to 16 show examples of surgical instruments used for the treatment for repairing a vertebral body compression fracture including a packing operation of the bone replacement material 1. However, it is to be noted that the surgical instruments that can be used for the treatment are not limited to the instruments shown in these drawings.

In connection with the drawings, it is to be noted that in FIGS. 4 to 8 and FIG. 10 the upper views are respectively perspective views of a vertebra viewed from the bottom thereof, in which a vertebral body is partially cut away, and the lower views in FIGS. 4 to 8 and FIG. 10 are respectively plan views of the vertebra. Hereinafter, in relation to the upper views in FIGS. 4 to 8 and FIG. 10, the left side and the right side will be referred to as the "distal end" and the "proximal end", respectively. Also, in relation to the upper views in FIGS. 4 to 8 and FIG. 10 and in relation to FIG. 11, the upper side and the lower side will be referred to as the "upper side (head side)" and the "lower side (leg side)", respectively; and the left side and the right side will be referred to as the "anterior side (ventral side)" and the "posterior side (dorsal side)", respectively.

Figure 4:
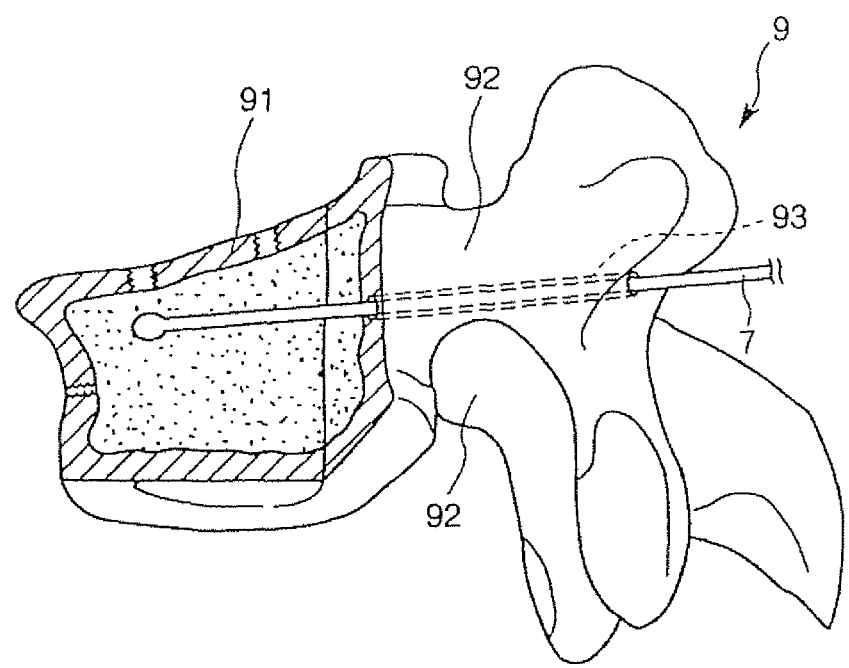
FIG. 4 includes schematic views for explaining a method of packing the bone replacement material into a vertebral body.
Figure 4:
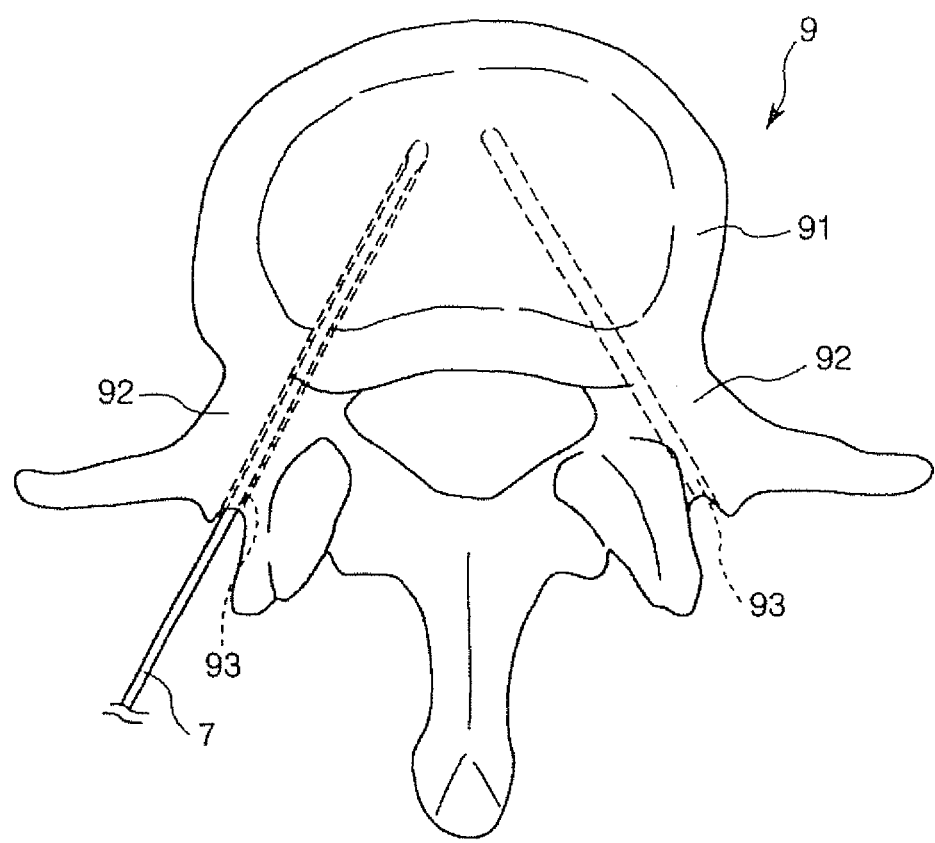

<1> First, as shown in FIG. 4, under X-ray guidance, a probe (a surgical instrument) 7 is pierced or inserted via each vertebral arch 92, 92 toward the targeted vertebral body 91 on each side of the vertebra 9 to which a treatment for repairing vertebral body compression fracture is carried out. Consequently, on both the left and right sides of the vertebra 9, paths 93, 93 are respectively formed so as to pass through the vertebral arch 92 into the vertebral body 91. Each of the paths 93, 93 has a small diameter.

Figure 12:
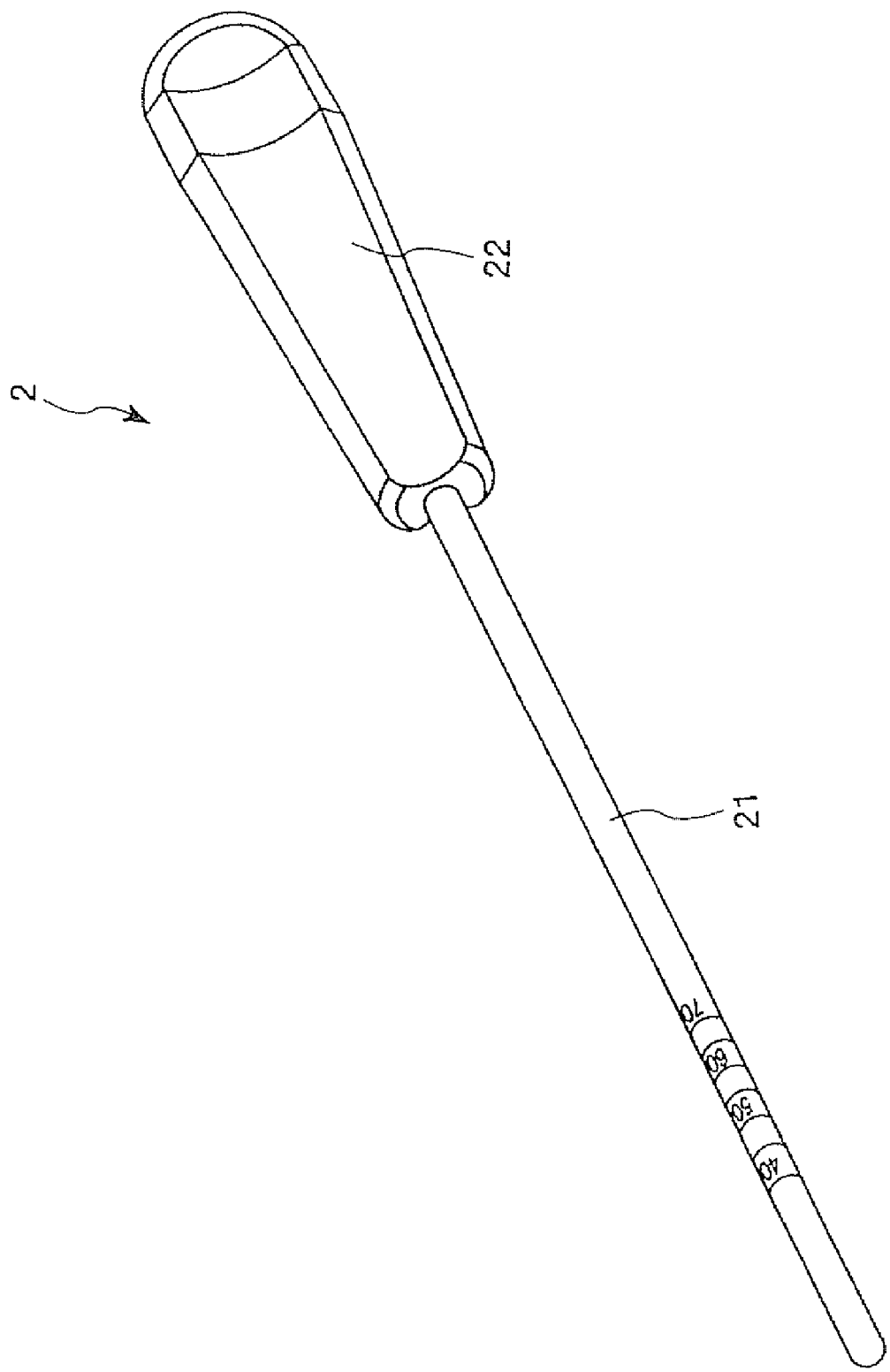
FIG. 12 is a perspective view which shows an example of a guide rod used for the treatment.

<2> Next, using a guide rod 2, the diameter of the path 93 is widened. As shown in FIG. 12, the guide rod 2 includes a rod-shaped portion 21 and a grip portion 22 mounted to a proximal end of the rod-shaped portion 21.

Figure 5:
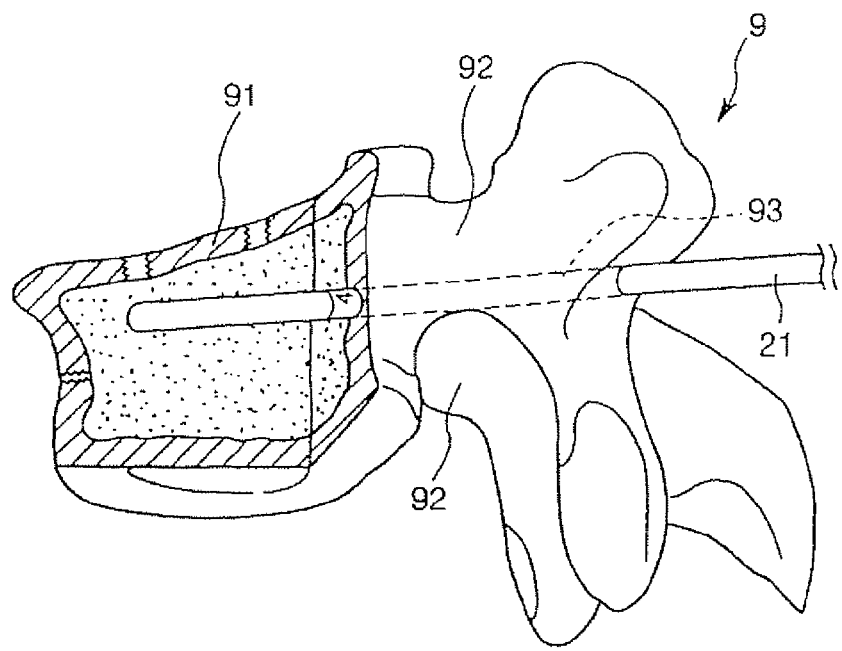
FIG. 5 includes schematic views for explaining the method of packing the bone replacement material into the vertebral body.
Figure 5:
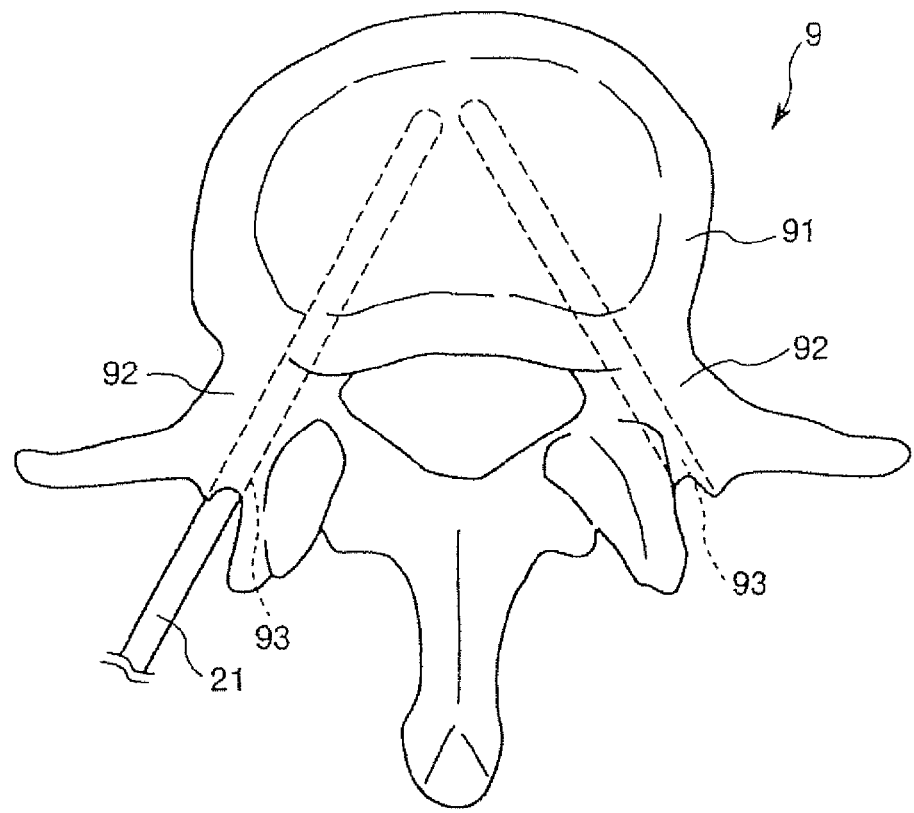

As shown in FIG. 5, an operator grips the grip portion 22 of the guide rod 2, and then inserts the distal end of the rod-shaped portion 21 into one of the paths 93, 93. In this way, the path 93 is widened.

In this regard, it is to be noted that two or more guide rods 2 are prepared, in which each rod-shaped portion 21 has a different outer diameter (e.g., three types of guide rods having an outer diameter of 4 mm, 5 mm, and 6 mm, respectively). By using these guide rods 2 in the order in which the outer diameter is increased, it is possible to widen the path 93 in multiple steps. Such an operation is performed on each of the paths 93 on the right and left sides.

<3> Next, using a vertical elevator 3, an upper portion of the vertebral body 91, in particular an upper anterior surface of the inside of the vertebral body 91 is returned (reduced) to a substantially normal position.

Figure 13:
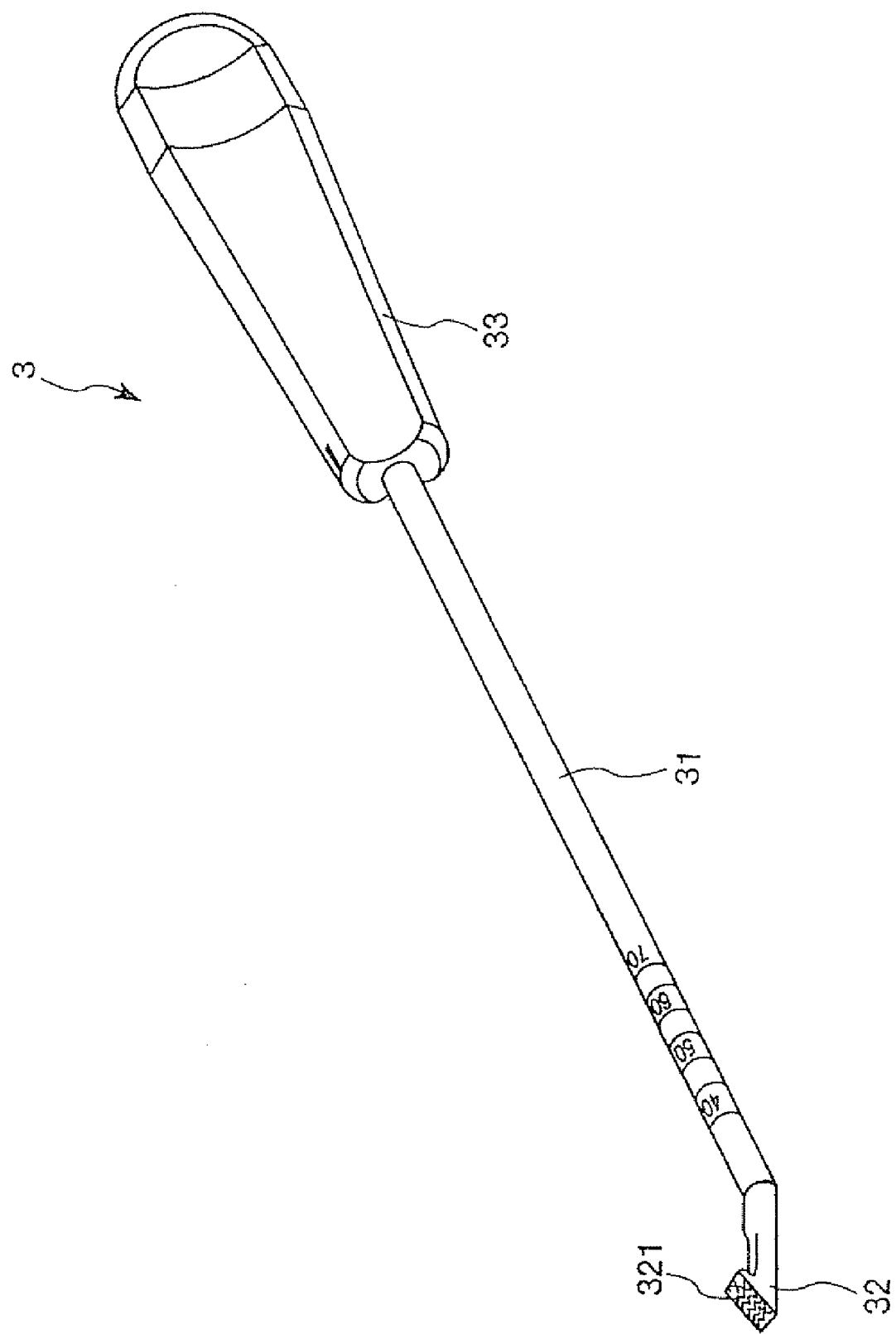
FIG. 13 is a perspective view which shows an example of a vertical elevator used for the treatment.

As shown in FIG. 13, the vertical elevator 3 includes a rod-shaped main body 31, a pushing portion 32 provided on the distal end of the rod-shaped main body 31 and a grip portion 33 provided on the proximal end of the rod-shaped main body 31.

Figure 6:
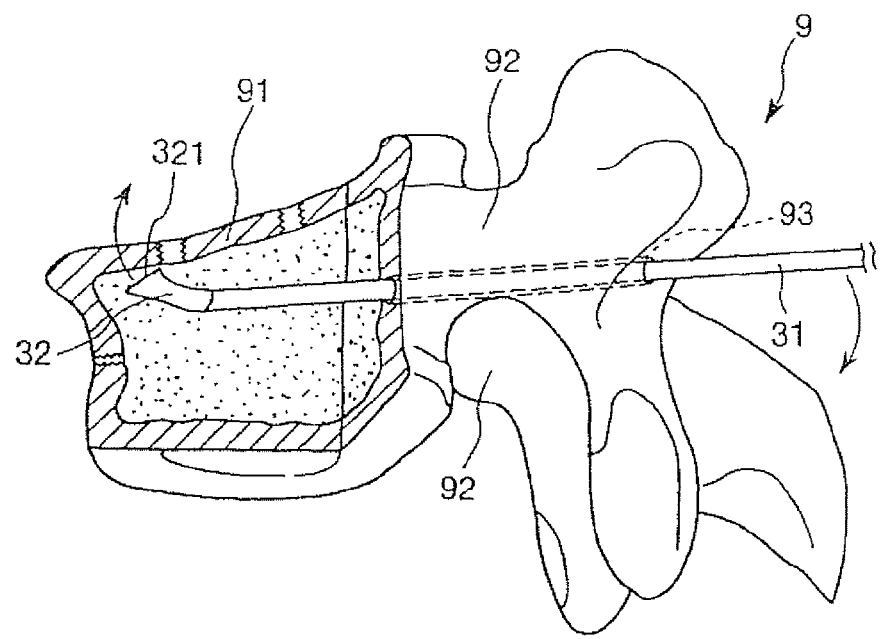
FIG. 6 includes schematic views for explaining the method of packing the bone replacement material into the vertebral body.
Figure 6:
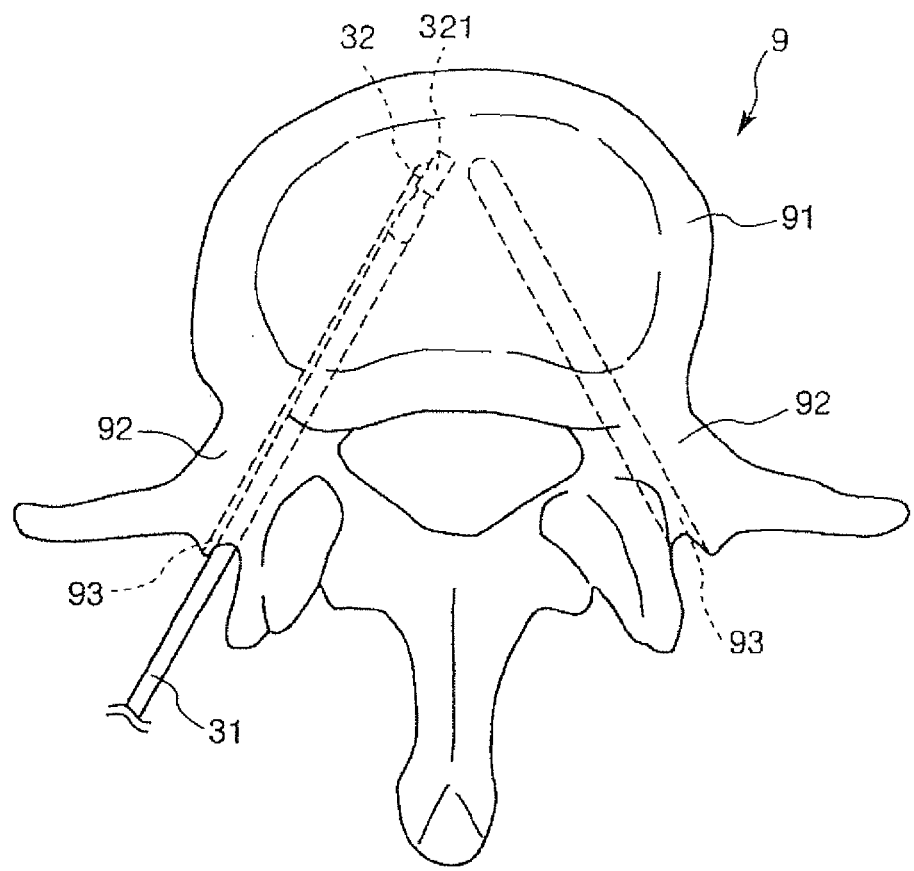

As shown in FIG. 6, the operator grips the grip portion 33 of the vertical elevator 3 to insert the distal end portion of the vertical elevator 3, including the pushing portion 32 and the distal end portion of the main body 31, into the vertebral body 91 through one of the paths 93 to position the pushing portion 32 in the anterior portion of the vertebral body 91. At this time, the distal end surface 321 of the pushing portion 32 is set so as to point in an upward direction.

Then, the proximal end portion of the main body 31 is pushed downwardly so that the distal end surface 321 of the pushing portion 32 comes into contact with the upper anterior surface of the inside of the vertebral body 91 and then the upper anterior portion of the vertebral body 91 is pushed upwardly. Consequently, the upper anterior portion of the vertebral body 91 is upwardly elevated.

When such an operation is complete, the distal end portion of the vertical elevator 3 is removed from the vertebra 9, and then the operator again inserts the vertical elevator 3 into the vertebral body 91 through the other path 93 to perform the same operation as described above.

<4> Next, using a horizontal elevator 4, an upper portion of a vertebra 91, in particular the upper middle portion of the inside of the vertebral body 91 is returned (reduced) to its normal position.

Figure 14:
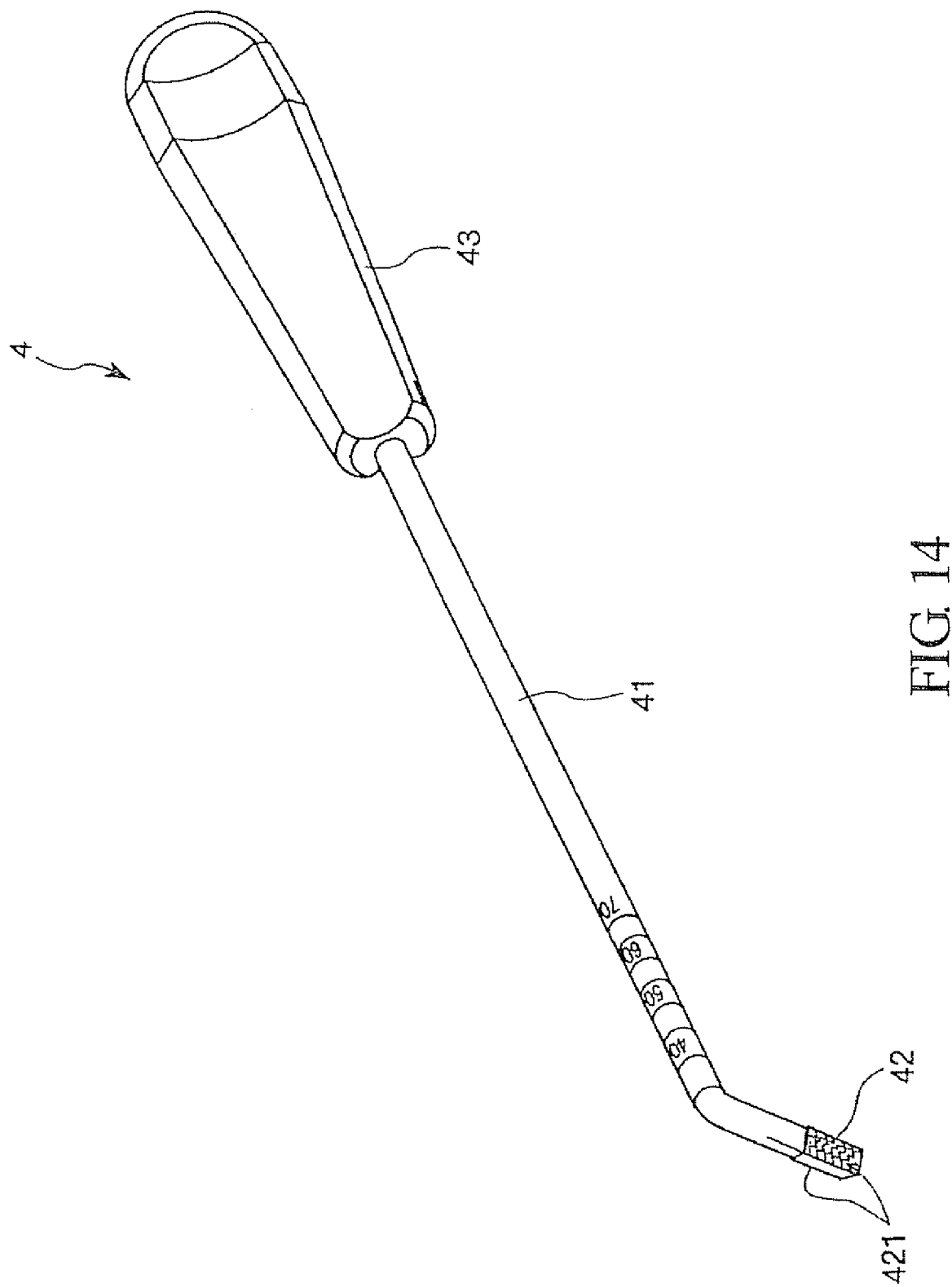
FIG. 14 is a perspective view which shows an example of a horizontal elevator used for the treatment.

As shown in FIG. 14, the horizontal elevator 4 includes a rod-shaped main body 41, a pushing portion 42 provided on the distal end of the main body 41 and a grip portion 43 provided on the proximal end of the rod-shaped main body 41.

Figure 7:
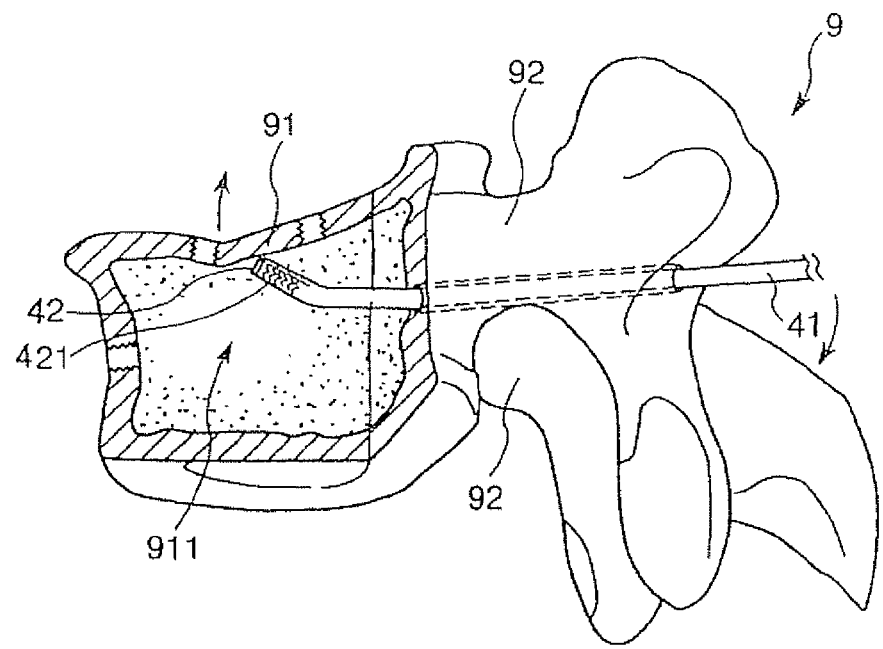
FIG. 7 includes schematic views for explaining the method of packing the bone replacement material into the vertebral body.
Figure 7:
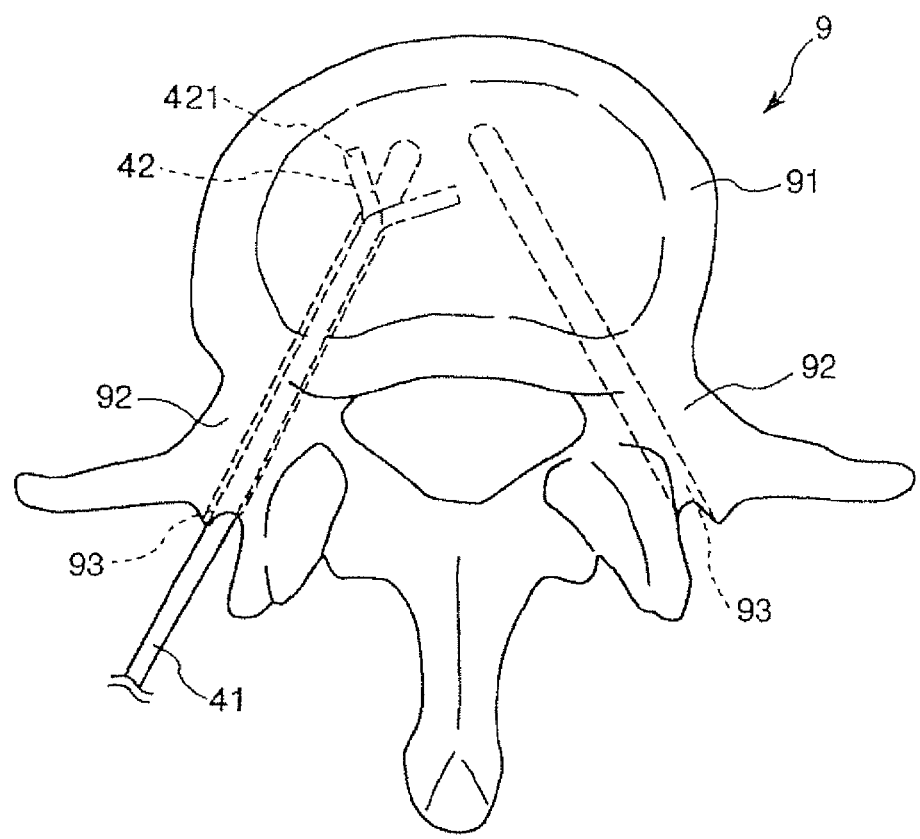

As shown in FIG. 7, the operator grips the grip portion 43 of the horizontal elevator 4 to insert the distal end portion of the horizontal elevator 4, including the pushing portion 42 and the distal end portion of the main body 41, into the vertebral body 91 through one of the paths 93 to position the pushing portion 42 in the middle portion of the vertebral body 91. At this time, one of the side surfaces 421 of the pushing portion 42 is set so as to point in an upward direction.

Then, the proximal end of the main body 41 is pushed downwardly so that the side surface 421 of the pushing portion 42 comes into contact with the upper middle surface of the inside of the vertebral body 91 and then the upper middle portion of the vertebral body 91 is pushed upwardly. Consequently, the upper middle portion of the vertebral body 91 is upwardly elevated.

Further, the pushing portion 42 is turned about an axis of the main body 41 by a prescribed angle, and then the same operation as described above is performed. In this way, it is possible to perform the reduction procedure on the upper middle portion of the vertebral body 91 over a wide range.

When such an operation is complete, the distal end portion of the horizontal elevator 4 is removed from the vertebra 9. Further, the operator again inserts the horizontal elevator 4 into the vertebral body 91 through the other path 93 to perform the same procedures as described above.

Each of the reduction procedures described in <3> and <4> is repeatedly performed two or more times until the vertebral body 91 is returned to a substantially normal shape.

In this regard, it is to be noted that the cavity 911 (a bone defective part) is created within the vertebral body 91 as a result of the reduction procedures mentioned above.

<5> Next, using an inserter (packing instrument) 5, a bone replacement material 1 in the form of a pellet is packed into the inside of the vertebra 91 of which shape has been returned to its original shape (that is, into the cavity 911 formed inside the vertebral 911 by the reduction procedure).

Figure 15:
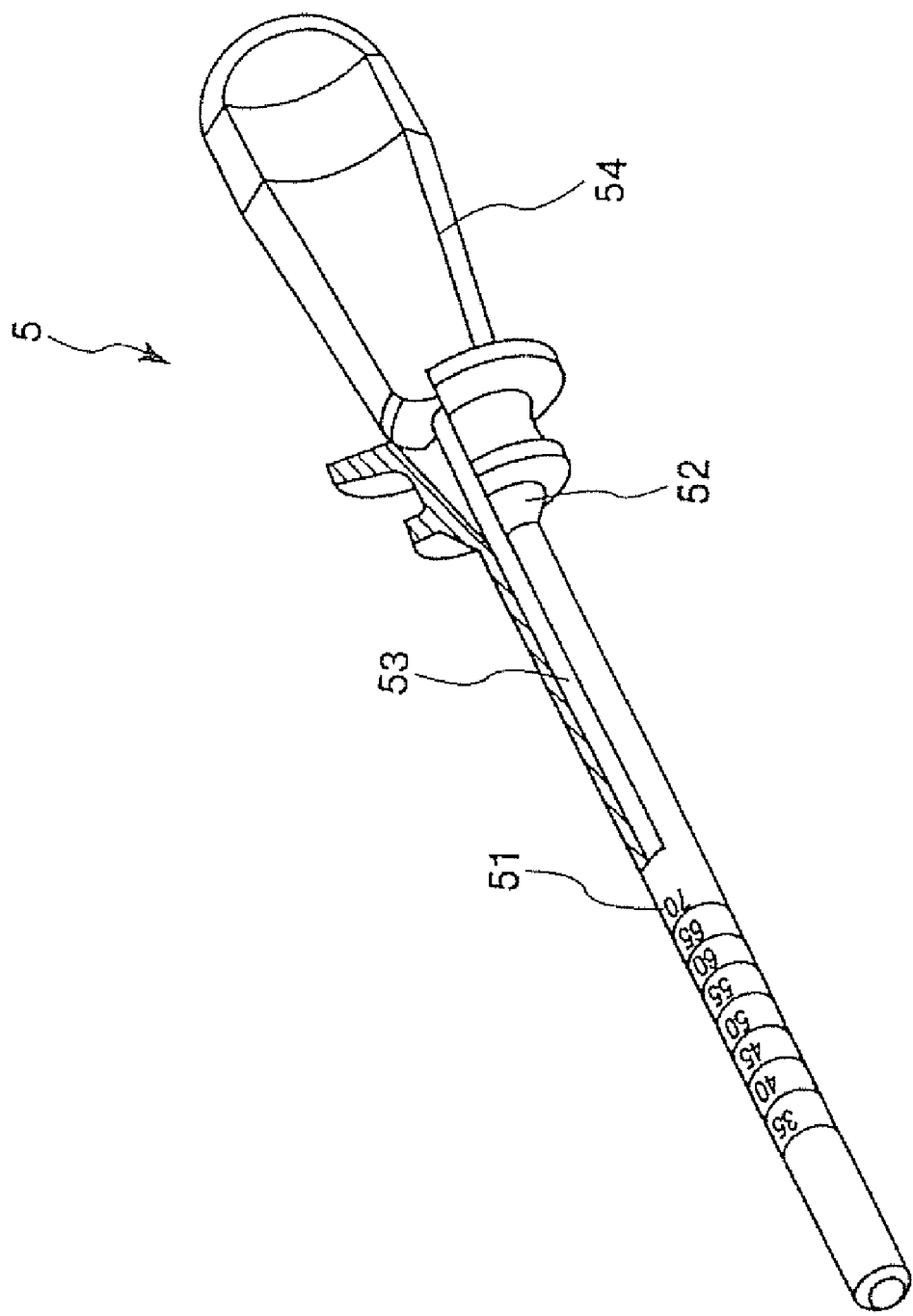
FIG. 15 is a perspective view which shows an example of an inserter used for the treatment.

As shown in FIG. 15, the inserter 5 includes a cylindrical member 51, an ejector bar 53 adapted to be inserted into a hollow passage of the cylindrical member 51, a cylindrical member grip portion 52 provided on the proximal end of the cylindrical member 51, and an ejector bar grip portion 54 provided on the proximal end of the ejector bar 53.

Figure 8:
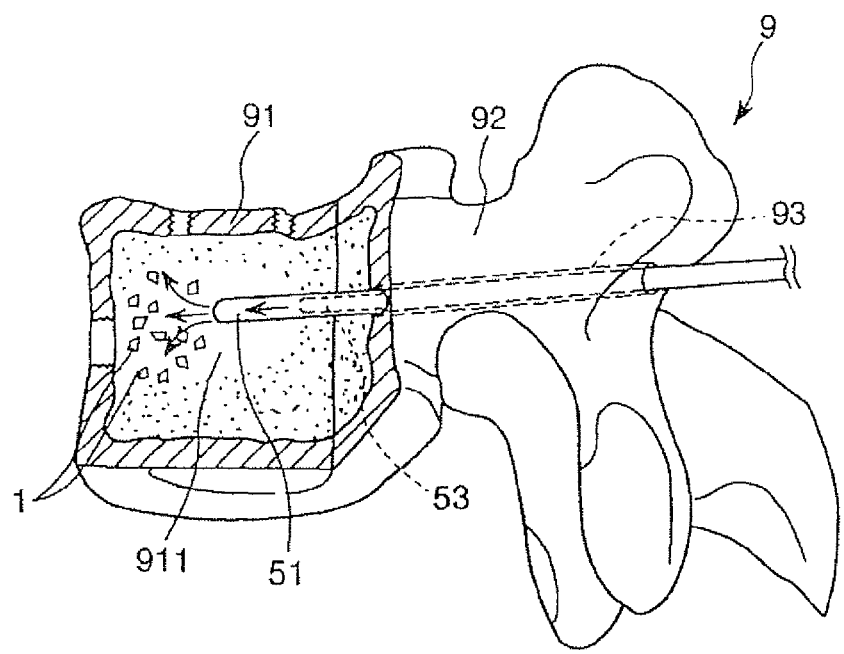
FIG. 8 includes schematic views for explaining the method of packing the bone replacement material into the vertebral body.
Figure 8:
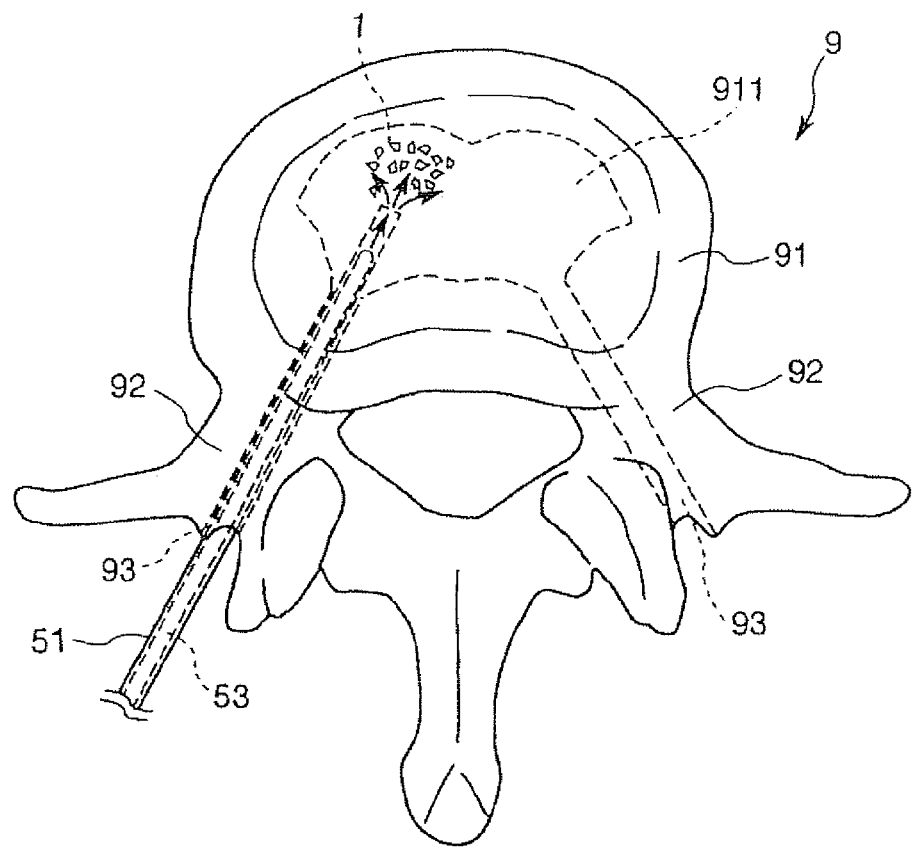

As shown in FIG. 8, the operator grips the cylindrical member grip portion 52 of the cylindrical member 51 of the inserter 5 to insert the distal end portion of the cylindrical member 51 into the vertebral body 91 through one of the paths 93, so that the distal end of the cylindrical member 51 is positioned at a desired position within the cavity 911.

While the operator maintains grip on the cylindrical member grip portion 52 with one hand to maintain the position of the distal end of the cylindrical member 51 within the vertebral body 91, a number of pellets of the bone replacement material 1 are Led into the passage of the cylindrical member 51 from the proximal end of the cylindrical member grip portion 52.

Then, the operator grips the ejector bar grip portion 54 of the ejector bar 53 with the other hand to insert the ejector bar 53 into the passage of the cylindrical member 51 from the proximal end of the cylindrical member grip portion 52 toward the distal end of the cylindrical member 51. By doing so, the pellets of the bone replacement material 1 placed in the passage of the cylindrical member 51 are pushed by the distal end of the ejector bar 53 toward the distal end of the cylindrical member 51.

By further pushing the ejector bar 53 toward the distal end of the cylindrical member 51, the distal end of the ejector bar 53 projects out of the distal end of the cylindrical member 51 so that the pellets of the bone replacement material are successively introduced into the cavity 91 and the cavity is filled with the pellets of the bone replacement material.

In this case, the bone replacement material 1 of the present invention is formed into a pellet having the above mentioned shape, the packing operation thereof into the vertebral body can be carried out smoothly, reliably and safely. In particular, in the above embodiments, each pellet of the bone replacement material 1 has the shape having an inclined surface as described above. Therefore, when the bone replacement material 1 is packed into the cavity 91 using the cylindrical member 51, the pellets of the bone replacement material 1 are pushed by the ejector bar 53 so that each pellet of the bone replacement material 1 is pushed out in a predetermined direction along the inclined surface of the adjacent pellet of the bone replacement material 1.

Specifically, each pellet of the bone replacement material 1 is formed into a roughly polyhedral shape which is defined by a plurality of surfaces including a pair of opposite surfaces, in which one of the opposite surfaces is inclined with respect to the other surface at a predetermined angle. When the pellets of the bone replacement material 1 are packed into a bone defective part, they are introduced and packed into the cavity 911 in the bone detective part using the cylindrical member 51 having a hollow passage. In this case, each pellet of the bone replacement material 1 is inserted into the hollow passage of the cylindrical member 51 such that its inclined surface faces the adjacent pellet (preferably, faces the inclined surface of the adjacent pellet), whereby each pellet of the bone replacement material 1 is adapted to be pushed out in various directions from the hollow passage of the cylindrical member 51 as shown in FIG. 9.

Figure 9:
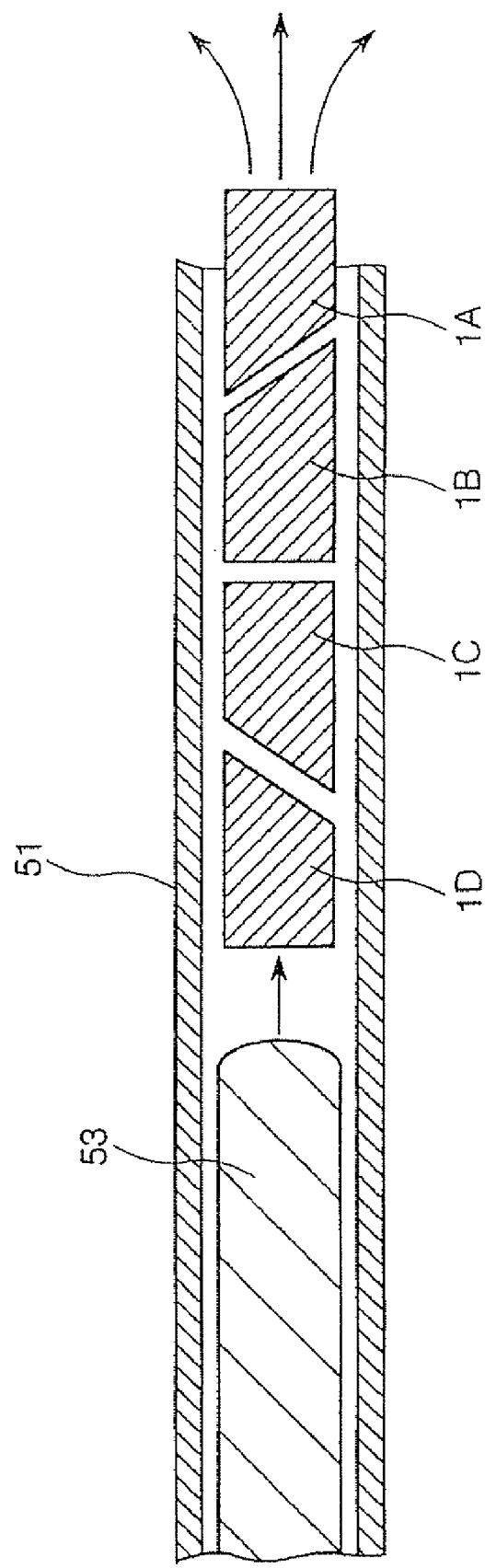
FIG. 9 is a cross sectional view for explaining the method of packing the bone replacement material into the vertebral body.

In more details, in the example shown in FIG. 9, the pellet 1A of the bone replacement material is pushed out upwardly in the drawing by the inclined surface of the adjacent pellet 1B. The pellet 1B of the bone replacement material is pushed out in a direction substantially parallel to the cylindrical member 51. Further, the pellet of the bone replacement material 1C is pushed out downwardly in the drawing by the adjacent pellet of the bone replacement material 1D.

Further, since the bone replacement material 1 has the shape as described above, when a plurality of pellets of the bone replacement material 1 are successively introduced into the vertebral body, the introduced pellets of the bone replacement material 1 are dispersed into various directions, thereby making it possible that the cavity 911 is filled with the pellets of the bone replacement material 1 uniformly. Further, since the bone replacement material that has been introduced into the cavity 911 does not remain near the opening of the cylindrical member 51, it is possible to pack a sufficient amount of the pellet-type bone replacement material 1.

Furthermore, since it is possible to prevent the hollow passage of the cylindrical member 51 from being clogged with the bone replacement material, it is possible to carry out the packing operation smoothly and reliably.

In this packing operation for packing the pellets of the bone replacement material 1 into the cavity 911, the maximum length of the ejector bar 53 projecting out from the distal end of the cylindrical member 51 is limited due to the abutment of the ejector bar grip portion 54 with the cylindrical member grip portion 52. Therefore, it is possible to prevent the ejector bar 53 From projecting out more than a necessary amount, thereby preventing the ejector bar 53 from pushing an unnecessary portion of the vertebral body 91, thus providing a high level of safety.

<6> Next, using an impactor 6, the density of the bone replacement material 1 packed in the vertebral body 91 which has been reduced is increased. According to this, the pellets of the bone replacement material 1 are aggregated in the vertebral body 91.

Figure 10:
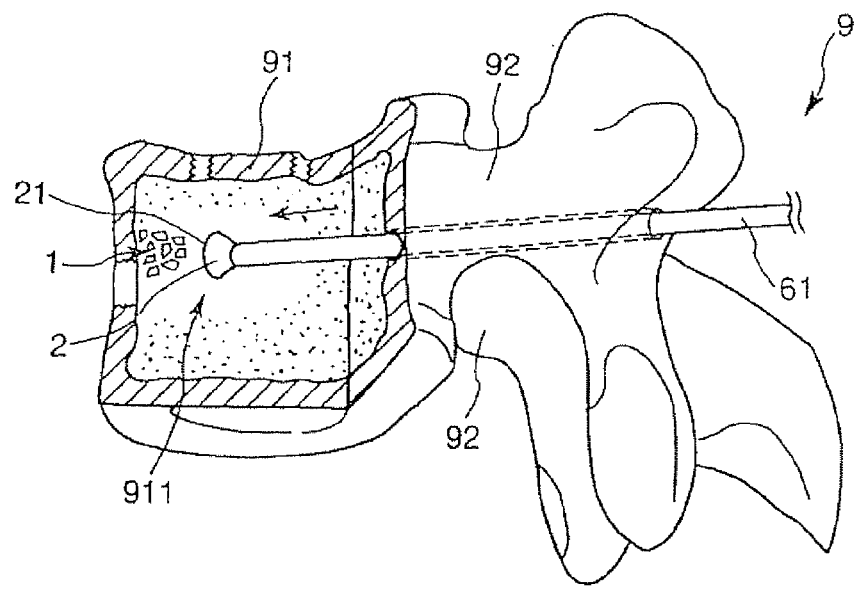
FIG. 10 includes schematic views for explaining the method of packing the bone replacement material into the vertebral body.
Figure 10:
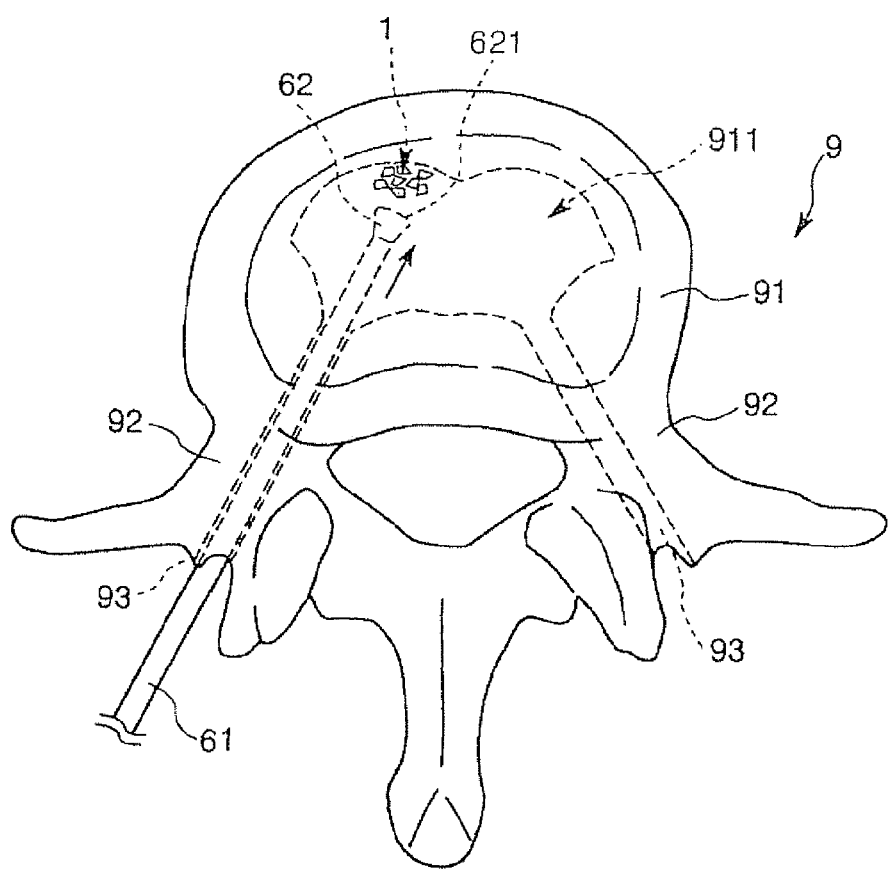
Figure 11:
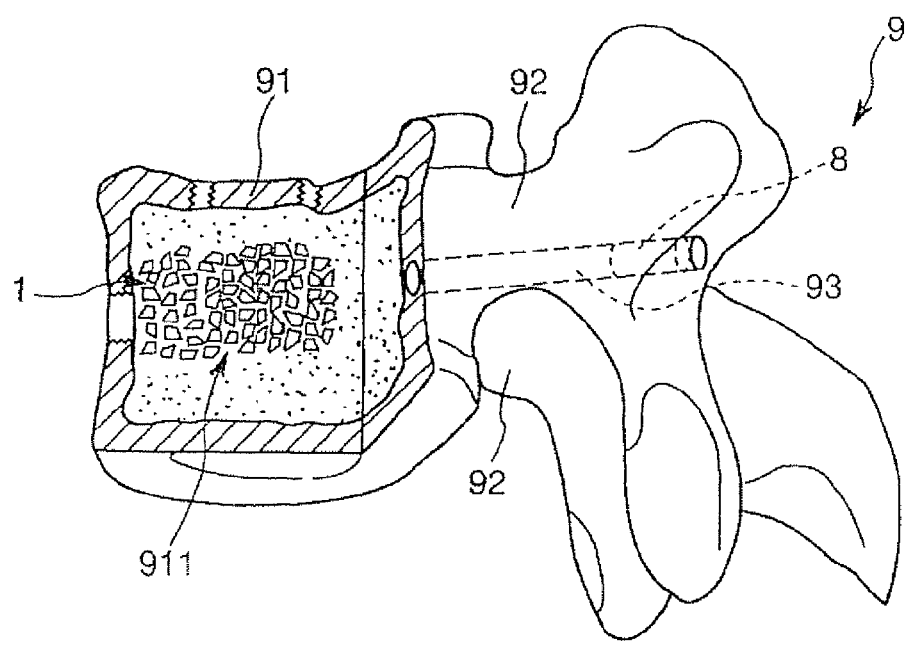
FIG. 11 is a schematic view of the vertebra to which the treatment for repairing a vertebral body compression fracture has been carried out.
Figure 16:
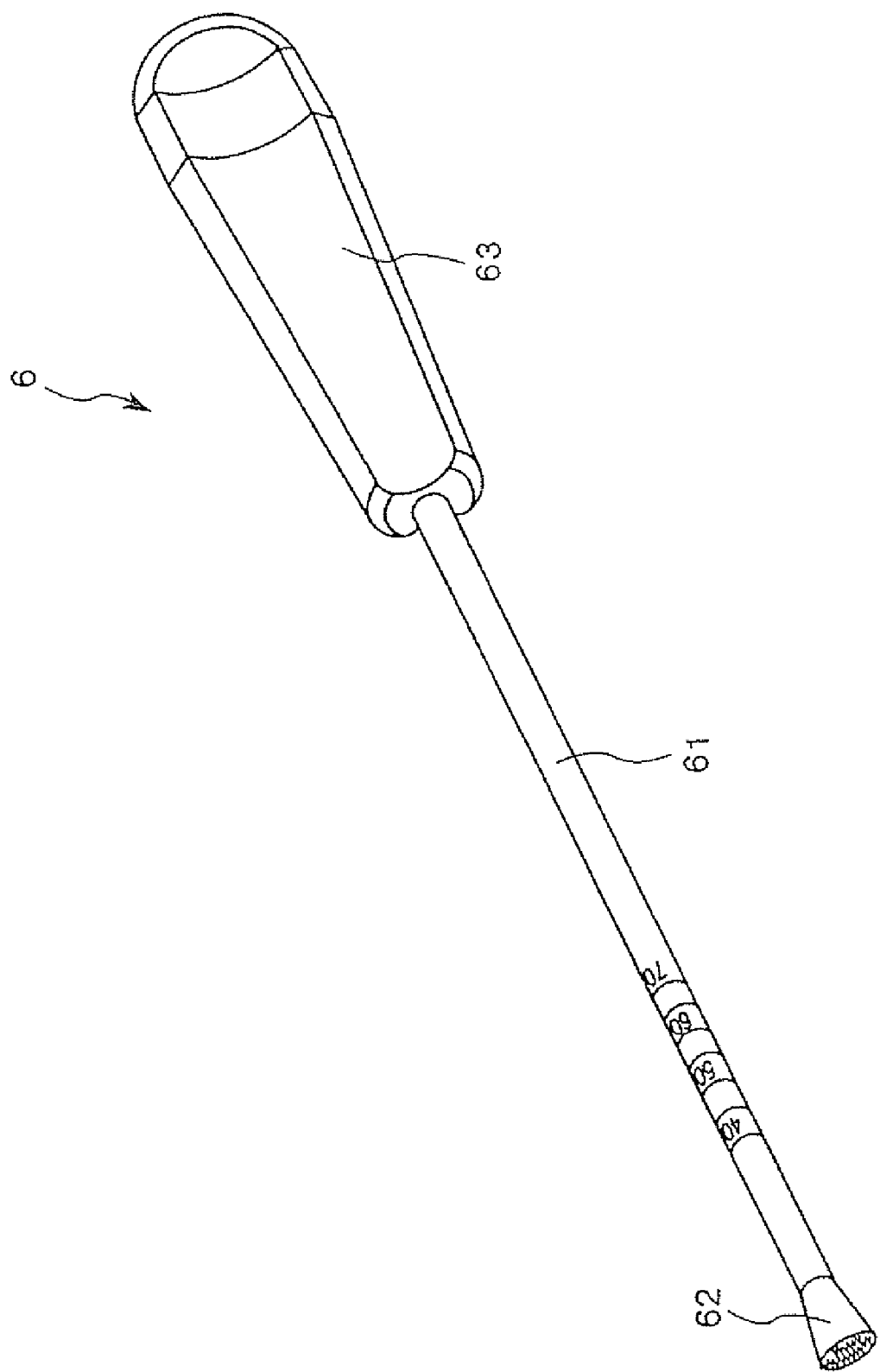
FIG. 16 is a perspective view which shows an example of an impactor used for the treatment.

As shown in FIGS. 10 and 16, the impactor 6 includes a rod-shaped main body 61, an impacting portion 62 provided on the distal end of the rod-shaped main body 61 and a grip portion 63 provided on the proximal end of the rod-shaped main body 61.

As shown in FIG. 10, the operator grips the grip portion 63 of the impactor 6 to insert the distal end portion of the impactor 6, including the impacting portion 62 and the distal end portion of the main body 61, into the vertebral body 91 through one of the paths 93.

Then, the pellets of the bone replacement material 1 introduced in the cavity 911 by the operation described in <5> are impacted by the impacting portion 62, thereby increasing the density (filling density) of the bone replacement material 1.

By repeatedly performing each of the operation for packing the bone replacement material 1 described in <5> and the operation for increasing the density of the bone replacement material 1 described in <6> two or more times through each of the paths 93 on the right and left sides, the cavity 911 created in the vertebral body 91 is filled with the bone replacement material 1 and its filling density is also increased. In this case, by using the pellet-type bone replacement material 1 having the inclined surface 11, this density increasing process can be more effectively carried out. This is because when the pellet-type bone replacement material is impacted by the impactor 6, the pellets of the bone replacement material 1 are pushed into a space in the cavity 911 with sliding each other at their inclined surfaces 11, thereby the cavity 911 is filled with the pellets of the bone replacement material 1 so as to have a high filling density.

By performing such operations described in <5> and <6>, the vertebral body 91 may be further reduced.

<7> Next, as shown in FIG. 11, each of the paths 93 on the right and left sides is sealed with a plug 8 made of a biomaterial such as hydroxyapatite or the like By doing so, it is possible to prevent the bone replacement material 1 from leaking out of the inside of the vertebral body 91 (cavity 911) through the paths 93, 93. Therefore, it is possible to prevent the vertebral body 91 from being collapsed again.

In this regard, it is to be noted that each of the paths 93 is sealed with, for example, a bone cement or the like instead of the plug 8.

Once all of the surgical procedures for the treatment of a compression fracture of the vertebral body 91 are complete, the operation site (incision site) is closed by suturing or ligation to finish the surgical operation.

According to this method, it is possible to carry out the surgical procedures for the treatment of a compression fracture of the vertebral body with less inversion.

As described above, each pellet of the bone replacement material 1 packed in the cavity of the vertebral body has a roughly polyhedral shape defined by a plurality of surfaces, the pellets of the bone replacement material 1 are packed in the cavity of the vertebral body in a state that they are surface to surface contact with each other so that they are stably placed. With this results a load withstanding capacity can be secured, and therefore if the bone replacement material 1 is used at a site where a load is likely to be applied, displacement of the pellets will hardly occur, so that satisfactory packing condition can be maintained.

Further, according to the bone replacement material of the present invention, the cavity of the vertebral body can be filled with the bone replacement material without leaving any space or gap, it is possible to suppress the decrease of the volume of the vertebral body after the operation, thereby enabling to maintain the result of the operation for a long period of time.

In the foregoing, the description was made with regard to the bone replacement material of the present invention based on the embodiments shown in the drawings. However, it should be understood that the present invention is not limited to the embodiments.

INDUSTRIAL UTILIZATION

As described above, according to the present invention, the packing operation of the bone replacement material can be carried out smoothly, reliably and safely.

Further, according to the present invention, it is possible to pack the bone replacement material to all portions of the bone defective part uniformly and sufficiently.

Furthermore, according to the present invention, since satisfactory packing condition can be maintained inside the bone defective part, it is possible to maintain the result of the operation for a long period of time.

Moreover, according to the present invention, since the bone replacement material is packed into a bone defective part using a cylindrical member having a hollow passage, it is possible to minimize skin incision and carry out a surgical procedure with less invasion.

Finally, it is to be understood that many changes and additions may be made to the embodiments described above without departing from the scope and spirit of the invention as defined in the following claims.

Further, it is also to be understood that the present disclosure relates to the subject matter contained in Japanese Patent Application No. 2003-410873 (filed on Dec. 9, 2003) which is expressly incorporated herein by reference in its entireties.

The invention claimed is:

1. A bone replacement material to be used by being packed into a bone defective part, wherein the bone replacement material consists essentially of a calcium phosphate based compound and is formed into a pellet and satisfies both of the following conditions (I) and (II):

(I) porosity is equal to or less than 75%; and
(II) collapsing strength is equal to or more than 15 Mpa, and wherein the pellet has a roughly polyhedral shape and,
wherein the pellet is defined by a plurality of surfaces including a pair of opposite, non-parallel surfaces and a surface adjoining to the pair of opposite, non-parallel surfaces, one of the opposite, non-parallel surfaces being inclined at a predetermined angle with respect to the other of the opposite, non-parallel surfaces, wherein the one of the opposite, non-parallel surfaces is non-adjoined with the other of the opposite, non-parallel surfaces in the pellet, and wherein the other of the opposite, non-parallel surfaces is perpendicular to the surface adjoining to the pair of opposite, non-parallel surfaces, wherein the predetermined angle is in the range of 20 to 40°, wherein the pellet of the roughly polyhedral shape is defined by a plurality of edges having different lengths, in which the length of the longest edge is in the range of 5 to 10 mm and the length of the shortest edge is in the range of 2 to 5 mm, wherein the volume of the pellet of the bone replacement material is in the range of 13 to 239 $mm^3$, wherein the bone replacement material is adapted to be packed into a cavity of the bone defective part using a cylindrical member having a hollow passage, wherein when a plurality of pellets of the bone replacement material are introduced and packed into the cavity in the bone defective part using the cylindrical member, each pellet of the bone replacement material is inserted into the hollow passage of the cylindrical member such that the inclined surface of the pellet faces the inclined surface of the adjacent pellet, whereby each pellet of the bone replacement material is pushed out in various directions from the hollow passage of the cylindrical member, wherein the plurality of pellets are configured to be pushed into the cavity in the bone defective part using the cylindrical member after being placed into the hollow passage of the cylindrical member, and wherein the pellet is formed free of a through hole being provided therethrough.

2. The bone replacement material as claimed in claim 1, wherein the pellet has a roughly prismatic shape.

3. The bone replacement material as claimed in claim 1, wherein the pellet has a roughly hexahedral shape.

4. The bone replacement material as claimed in claim 3, wherein the pellet is formed into a rectangular solid, a part of which is cut off.

5. The bone replacement material as claimed in claim 1, wherein the pellet has a roughly pentahedral shape.

6. The bone replacement material as claimed in claim 5, wherein the pellet is formed into a triangular prism shape, a part of which is cut off.

7. The bone replacement material as claimed in claim 1, wherein the roughly polyhedral shape has a circumferential surface and two side surfaces.

8. The bone replacement material as claimed in claim 7, wherein the pellet is formed into a cylinder solid, a part of which is cut off.

9. The bone replacement material as claimed in claim 1, wherein each pellet of the bone replacement material has been subjected to a chamfering processing.

10. The bone replacement material as claimed in claim 1, wherein the Ca/P ratio of the calcium phosphate based compound is in the range of 1.0 to 2.0.

11. The bone replacement material as claimed in claim 1, wherein the bone replacement material is adapted to be packed into a bone defective part formed in one or more bones such as vertebral body, ilium, scapula, humerus, ulna, radius, femur, tibia and fibula.

12. The bone replacement material as claimed in claim 11, wherein, when a plurality of pellets of the bone replacement material are introduced and packed into a cavity in the bone defective part using a cylindrical member having a hollow passage, each pellet of the bone replacement material is inserted into the hollow passage of the cylindrical member such that the inclined surface of the pellet faces the inclined surface of the adjacent pellet, whereby each pellet of the bone replacement material is pushed out in various directions from the hollow passage of the cylindrical member, wherein each of the plurality of pellets is free of a through hole being provided therethrough, and wherein the plurality of pellets are configured to be pushed into the cavity in the bone defective part using the cylindrical member after being placed into the hollow passage of the cylindrical member.

* * * * *